US011450230B2

(12) United States Patent
Lim et al.

(10) Patent No.: US 11,450,230 B2
(45) Date of Patent: Sep. 20, 2022

(54) ELECTRONIC DEVICE INCLUDING MEDITATION APPLICATION

(71) Applicant: Samsung Electronics Co., Ltd., Gyeonggi-do (KR)

(72) Inventors: Jinmook Lim, Gyeonggi-do (KR); Seunggu Kang, Gyeonggi-do (KR); Hyogil Kim, Gyeonggi-do (KR); Haebahremahram Suh, Gyeonggi-do (KR); Kumhwa Baek, Gyeonggi-do (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 155 days.

(21) Appl. No.: 16/784,379

(22) Filed: Feb. 7, 2020

(65) Prior Publication Data

US 2020/0265744 A1 Aug. 20, 2020

(30) Foreign Application Priority Data

Feb. 19, 2019 (KR) .................. 10-2019-0019441

(51) Int. Cl.
*G09B 5/06* (2006.01)
*G09B 19/00* (2006.01)

(52) U.S. Cl.
CPC ............. *G09B 19/003* (2013.01); *G09B 5/06* (2013.01)

(58) Field of Classification Search
CPC ........ G09B 5/06; G09B 19/003; A41D 1/002; A61B 2560/0214; A61B 2562/0219;
(Continued)

(56) References Cited

U.S. PATENT DOCUMENTS 9,138,558 B1 9/2015 Kusik et al.
9,402,581 B2 8/2016 Kusik et al.
(Continued)

FOREIGN PATENT DOCUMENTS

JP 2019-000497 A 1/2019
KR 10-2010-0040431 A 4/2010
(Continued)

OTHER PUBLICATIONS

International Search Report dated Jun. 4, 2020.
European Search Report dated Jun. 24, 2020.

*Primary Examiner* — Milap Shah
(74) *Attorney, Agent, or Firm* — Cha & Reiter, LLC

(57) ABSTRACT

An electronic device includes a user interface; a wireless communication circuit configured to communicate with an external electronic device; a processor; and a memory electrically connected to the processor. The memory stores instructions that, when executed by the processor, cause the processor to: identify a user input to start a meditation program via the user interface; start the meditation program in response to the identified user input; receive data related to a stress level of a user measured by the external electronic device during execution of the meditation program from the external electronic device via the wireless communication circuit; and display visual information on the user interface, wherein the visual information visually indicates a stress level change of the user resulting from the execution of the meditation program, based on at least a portion of the received data. In addition, various embodiments identified herein are realized.

16 Claims, 15 Drawing Sheets

(58) Field of Classification Search
CPC ....... A61B 5/01; A61B 5/02055; A61B 5/024; A61B 5/0402; A61B 5/04085; A61B 5/1118; A61B 5/14552; A61B 5/6802; A61B 5/6832

See application file for complete search history.

(56) References Cited

U.S. PATENT DOCUMENTS

| | | | |
|---|---|---|---|
| 9,668,693 B2 | 6/2017 | Kusik et al. | |
| 9,711,060 B1 * | 7/2017 | Lusted | A61B 5/02416 |
| 10,186,163 B1 * | 1/2019 | Letterese | G09B 19/00 |
| 2011/0124996 A1 | 5/2011 | Reinke et al. | |
| 2015/0199010 A1 * | 7/2015 | Coleman | A61B 5/369 |
| | | | 345/156 |
| 2015/0339363 A1 | 11/2015 | Moldoveanu et al. | |
| 2015/0351655 A1 | 12/2015 | Coleman | |
| 2015/0366502 A1 | 12/2015 | Kusik et al. | |
| 2016/0005320 A1 * | 1/2016 | deCharms | A61B 8/0808 |
| | | | 434/236 |
| 2016/0166197 A1 * | 6/2016 | Venkatraman | A61B 5/0816 |
| | | | 600/595 |
| 2016/0310073 A1 | 10/2016 | Kusik et al. | |
| 2017/0000348 A1 * | 1/2017 | Karsten | G16H 10/60 |
| 2017/0188976 A1 * | 7/2017 | Kalra | G16H 10/20 |
| 2017/0251967 A1 * | 9/2017 | Premsukh | A61B 5/02405 |
| 2017/0265805 A1 | 9/2017 | Kusik et al. | |
| 2017/0333666 A1 * | 11/2017 | Goldberg | A61B 5/6801 |
| 2019/0254590 A1 | 8/2019 | Venkatraman et al. | |
| 2020/0077942 A1 * | 3/2020 | Youngblood | A61B 5/4812 |
| 2021/0319875 A1 * | 10/2021 | Kim | A61M 21/02 |

FOREIGN PATENT DOCUMENTS

| | | | | |
|---|---|---|---|---|
| KR | 1904505 B1 | 10/2018 | | |
| WO | WO-2019138382 A1 * | 7/2019 | ........... | A61B 5/0002 |

* cited by examiner

ELECTRONIC DEVICE INCLUDING MEDITATION APPLICATION

CROSS-REFERENCE TO RELATED APPLICATION(S)

This application is based on and claims priority under 35 U.S.C. § 119 to Korean Patent Application No. 10-2019-0019441, filed on Feb. 19, 2019, in the Korean Intellectual Property Office, the disclosure of which is incorporated by reference herein its entirety.

BACKGROUND

1. Field

One or more embodiments disclosed in the instant disclosure generally relate to an electronic device that includes a meditation application.

2. Description of Related Art

Meditation is an activity that induces a conscious state so that an individual may train the mind to participate in peaceful thinking. Meditation may often clear the mind, reduce stress, promote rest, or train the mind. An electronic device may provide a meditation application that helps the user to perform the meditation.

Further, the electronic device may use a sensor to measure the user's various biometric signals. The biometric signals may include, for example, heart rate, oxygen saturation, blood pressure, blood sugar, etc. In one example, the electronic device may use a biometric sensor such as a PPG (photoplethysmography) sensor to measure the biometric signals.

The above information is presented as background information only to assist with an understanding of the disclosure. No determination has been made, and no assertion is made, as to whether any of the above might be applicable as prior art with regard to the disclosure.

SUMMARY

Aspects of the disclosure are to address at least the above-mentioned problems and/or disadvantages and to provide at least the advantages described below. Accordingly, various embodiments disclosed in the disclosure are to provide an electronic device that provides an integrated service for a meditation program and a stress measurement.

In accordance with an aspect of the disclosure, an electronic device includes a user interface; a wireless communication circuit configured to communicate with an external electronic device; a processor electrically connected to the user interface and the wireless communication circuit; and a memory electrically connected to the processor. The memory stores instructions that, when executed by the processor, cause the processor to: identify a user input to start a meditation program via the user interface; start the meditation program in response to the identified user input; receive data related to a stress level of a user measured by the external electronic device during execution of the meditation program from the external electronic device via the wireless communication circuit; and display visual information on the user interface, wherein the visual information visually indicates a stress level change of the user resulting from the execution of the meditation program, based on at least a portion of the received data.

In accordance with another aspect of the disclosure, a method for providing a meditation program by an electronic device includes identifying a user input to start a meditation program via a user interface of the electronic device; starting the meditation program in response to the identified user input; receiving data related to a stress level of the user measured by an external electronic device during execution of the meditation program from the external electronic device via a wireless communication circuit of the electronic device; and displaying visual information on the user interface, wherein the visual information visually indicates a stress level change of the user resulting from the execution of the meditation program, based on at least a portion of the received data.

Other aspects, advantages, and salient features of the disclosure will become apparent to those skilled in the art from the following detailed description, which, taken in conjunction with the annexed drawings, discloses various embodiments of the disclosure.

BRIEF DESCRIPTION OF THE DRAWINGS

The above and other aspects, features, and advantages of certain embodiments of the disclosure will be more apparent from the following description taken in conjunction with the accompanying drawings, in which.

In connection with the description of the drawings, the same or similar reference numerals may be used for the same or similar components.

DETAILED DESCRIPTION

Hereinafter, various embodiments of the disclosure are described with reference to the accompanying drawings.

However, the embodiments are not intended to limit a scope of the disclosure. It is to be understood that the various modifications, equivalents, and/or alternatives of the embodiments of the disclosure may be included in the scope of the disclosure.

Hereinafter, referring to FIG. 1 and FIG. 2, components included in an electronic device according to an embodiment will be described.

Certain embodiments disclosed in the instant disclosure may provide an electronic device that may receive the result of measuring the user's stress while a meditation program is executed, and may identify, based on the result, whether or not the stress is reduced using the meditation program.

Certain embodiments disclosed in the instant disclosure may provide an electronic device for measuring posture or movement of the user before starting a meditation program or during the meditation program, and thus inducing the correct posture for meditation.

Certain embodiments disclosed in the instant disclosure may provide an electronic device that informs the user of how his or her movement affects stress while a meditation program is executed.

Figure 1:
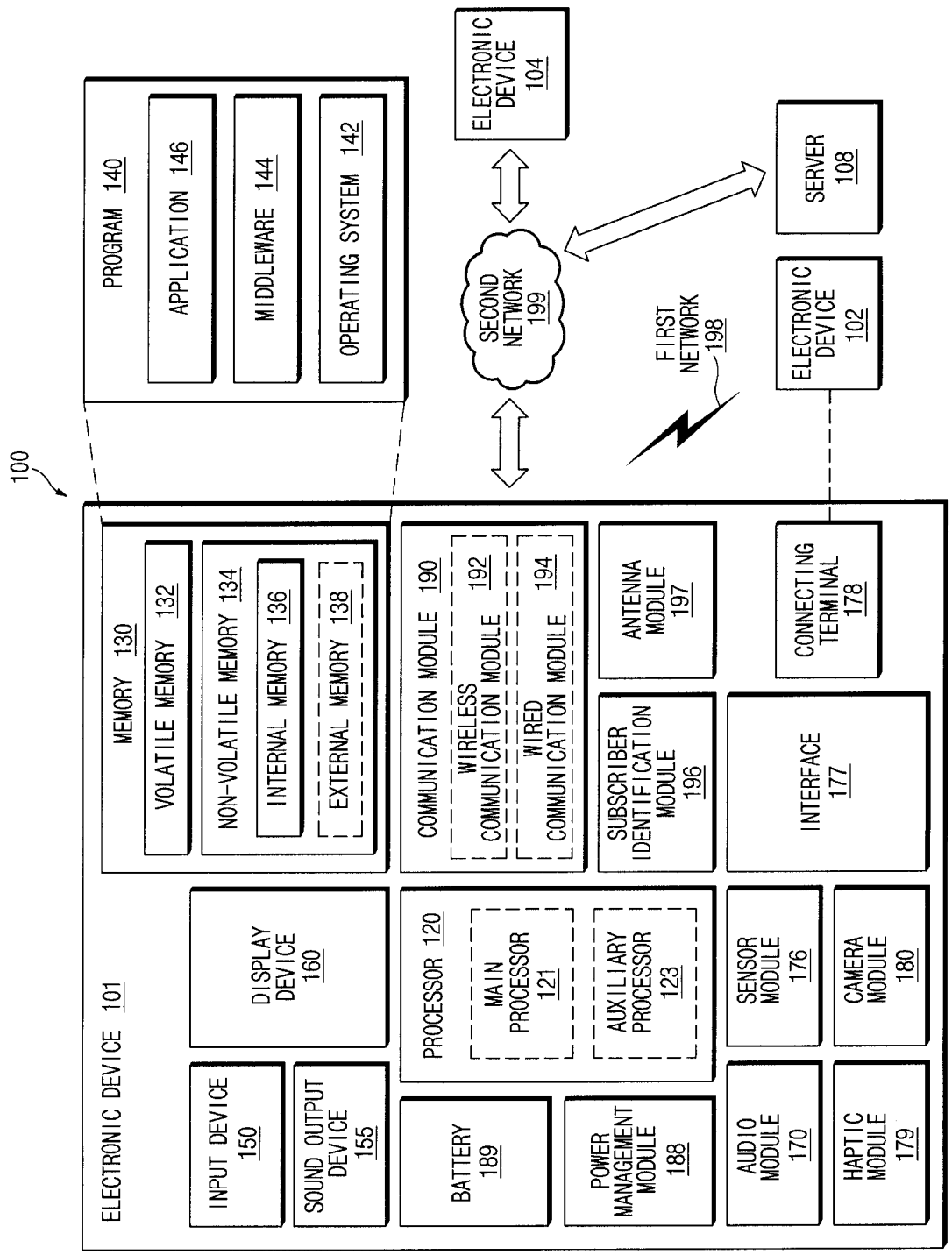
FIG. 1 is a block diagram of an electronic device in a network environment according to various embodiments.

FIG. 1 is a block diagram of an electronic device in a network environment according to various embodiments. FIG. 2 is a block diagram of a sensor module of the electronic device of FIG. 1.

FIG. 1 is a block diagram illustrating a first electronic device 101 in a network environment 100 according to various embodiments. Referring to FIG. 1, the first electronic device 101 in the network environment 100 may communicate with a first wearable electronic device 102 via a first network 198 (e.g., a short-range wireless communication network), or an second wearable electronic device 103 or a server 108 via a second network 199 (e.g., a long-range wireless communication network). According to an embodiment, the first electronic device 101 may communicate with the second wearable electronic device 103 via the server 108. According to an embodiment, the first electronic device 101 may include a processor 120, memory 130, an input device 150, a sound output device 155, a display device 160, an audio module 170, a sensor module 176, an interface 177, a haptic module 179, a camera module 180, a power management module 188, a battery 189, a communication module 190, a subscriber identification module (SIM) 196, or an antenna module 197. In some embodiments, at least one (e.g., the display device 160 or the camera module 180) of the components may be omitted from the first electronic device 101, or one or more other components may be added in the first electronic device 101. In some embodiments, some of the components may be implemented as single integrated circuitry. For example, at least one sensor included in the sensor module 176 may be implemented as embedded in the display device 160 (e.g., a display).

The processor 120 may execute, for example, software (e.g., a program 140) to control at least one other component (e.g., a hardware or software component) of the first electronic device 101 coupled with the processor 120, and may perform various data processing or computation. According to one embodiment, as at least part of the data processing or computation, the processor 120 may load a command or data received from another component (e.g., the sensor module 176 or the communication module 190) in volatile memory 132, process the command or the data stored in the volatile memory 132, and store resulting data in nonvolatile memory 134. According to an embodiment, the processor 120 may include a main processor 121 (e.g., a central processing unit (CPU) or an application processor (AP)), and an auxiliary processor 123 (e.g., a graphics processing unit (GPU), an image signal processor (ISP), a sensor hub processor, or a communication processor (CP)) that is operable independently from, or in conjunction with, the main processor 121. Additionally or alternatively, the auxiliary processor 123 may be adapted to consume less power than the main processor 121, or to be specific to a specified function. The auxiliary processor 123 may be implemented as separate from, or as part of the main processor 121.

The auxiliary processor 123 may control at least some of functions or states related to at least one component (e.g., the display device 160, the sensor module 176, or the communication module 190) among the components of the first electronic device 101, instead of the main processor 121 while the main processor 121 is in an inactive (e.g., sleep) state, or together with the main processor 121 while the main processor 121 is in an active state (e.g., executing an application). According to an embodiment, the auxiliary processor 123 (e.g., an image signal processor or a communication processor) may be implemented as part of another component (e.g., the camera module 180 or the communication module 190) functionally related to the auxiliary processor 123.

The memory 130 may store various data used by at least one component (e.g., the processor 120 or the sensor module 176) of the first electronic device 101. The various data may include, for example, software (e.g., the program 140) and input data or output data for a command related thereto. The memory 130 may include the volatile memory 132 or the nonvolatile memory 134.

The program 140 may be stored in the memory 130 as software, and may include, for example, an operating system (OS) 142, middleware 144, or an application 146. The application 146 may include an meditation application The input device 150 may receive a command or data to be used by other component (e.g., the processor 120) of the first electronic device 101, from the outside (e.g., a user) of the first electronic device 101. The input device 150 may include, for example, a microphone, a mouse, a keyboard, or a digital pen (e.g., a stylus pen).

The sound output device 155 may output sound signals to the outside of the first electronic device 101. The sound output device 155 may include, for example, a speaker or a receiver. The speaker may be used for general purposes, such as playing multimedia or playing record, and the receiver may be used for an incoming calls. According to an embodiment, the receiver may be implemented as separate from, or as part of the speaker.

The display device 160 may visually provide information to the outside (e.g., a user) of the first electronic device 101. The display device 160 may include, for example, a display, a hologram device, or a projector and control circuitry to control a corresponding one of the display, hologram device, and projector. According to an embodiment, the display device 160 may include touch circuitry adapted to detect a touch, or sensor circuitry (e.g., a pressure sensor) adapted to measure the intensity of force incurred by the touch.

The audio module 170 may convert a sound into an electrical signal and vice versa. According to an embodiment, the audio module 170 may obtain the sound via the input device 150, or output the sound via the sound output device 155 or a headphone of an external electronic device (e.g., an first wearable electronic device 102 or an second wearable electronic device 103) directly (e.g., wiredly) or wirelessly coupled with the first electronic device 101.

The sensor module 176 may detect an operational state (e.g., power or temperature) of the first electronic device 101 or an environmental state (e.g., a state of a user) external to the first electronic device 101, and then generate an electrical signal or data value corresponding to the detected state. According to an embodiment, configurations of the sensor module 176 will be described in detail with reference to FIG. 2.

The interface 177 may support one or more specified protocols to be used for the first electronic device 101 to be coupled with the external electronic device (e.g., the first wearable electronic device 102 or the second wearable electronic device 103) directly (e.g., wiredly) or wirelessly. According to an embodiment, the interface 177 may include, for example, a high definition multimedia interface (HDMI), a universal serial bus (USB) interface, a secure digital (SD) card interface, or an audio interface.

A connecting terminal 178 may include a connector via which the first electronic device 101 may be physically connected with the external electronic device (e.g., the first wearable electronic device 102). According to an embodiment, the connecting terminal 178 may include, for example, a HDMI connector, a USB connector, a SD card connector, or an audio connector (e.g., a headphone connector).

The haptic module 179 may convert an electrical signal into a mechanical stimulus (e.g., a vibration or a movement) or electrical stimulus which may be recognized by a user via his tactile sensation or kinesthetic sensation. According to an embodiment, the haptic module 179 may include, for example, a motor, a piezoelectric element, or an electric stimulator.

The camera module 180 may capture a still image or moving images. According to an embodiment, the camera module 180 may include one or more lenses, image sensors, image signal processors, or flashes.

The power management module 188 may manage power supplied to the first electronic device 101. According to one embodiment, the power management module 188 may be implemented as at least part of, for example, a power management integrated circuit (PMIC).

The battery 189 may supply power to at least one component of the first electronic device 101. According to an embodiment, the battery 189 may include, for example, a primary cell which is not rechargeable, a secondary cell which is rechargeable, or a fuel cell.

The communication module 190 may support establishing a direct (e.g., wired) communication channel or a wireless communication channel between the first electronic device 101 and the external electronic device (e.g., the first wearable electronic device 102, the second wearable electronic device 103, or the server 108) and performing communication via the established communication channel. The communication module 190 may include one or more communication processors that are operable independently from the processor 120 (e.g., the application processor (AP)) and supports a direct (e.g., wired) communication or a wireless communication. According to an embodiment, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device via the first network 198 (e.g., a short-range communication network, such as Bluetooth™, wireless-fidelity (Wi-Fi) direct, or infrared data association (IrDA)) or the second network 199 (e.g., a long-range communication network, such as a cellular network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 192 may identify and authenticate the first electronic device 101 in a communication network, such as the first network 198 or the second network 199, using subscriber information (e.g., international mobile subscriber identity (IMSI)) stored in the subscriber identification module 196.

The antenna module 197 may transmit or receive a signal or power to or from the outside (e.g., the external electronic device) of the first electronic device 101. According to an embodiment, the antenna module 197 may include an antenna including a radiating element composed of a conductive material or a conductive pattern formed in or on a substrate (e.g., PCB). According to an embodiment, the antenna module 197 may include a plurality of antennas. In such a case, at least one antenna appropriate for a communication scheme used in the communication network, such as the first network 198 or the second network 199, may be selected, for example, by the communication module 190 (e.g., the wireless communication module 192) from the plurality of antennas. The signal or the power may then be transmitted or received between the communication module 190 and the external electronic device via the selected at least one antenna. According to an embodiment, another component (e.g., a radio frequency integrated circuit (RFIC)) other than the radiating element may be additionally formed as part of the antenna module 197.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the first electronic device 101 and the external second wearable electronic device 103 via the server 108 coupled with the second network 199. Each of the wearable electronic devices 102 and 103 may be a device of a same type as, or a different type, from the first electronic device 101. According to an embodiment, all or some of operations to be executed at the first electronic device 101 may be executed at one or more of the external electronic devices 102, 103, or 108. For example, if the first electronic device 101 should perform a function or a service automatically, or in response to a request from a user or another device, the first electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the first electronic device 101. The first electronic device 101 may provide the outcome, with or without further processing of the outcome, as at least part of a reply to the request. To that end, a cloud computing, distributed computing, or client-server computing technology may be used, for example.

The electronic device according to various embodiments may be one of various types of electronic devices. The electronic devices may include, for example, a portable communication device (e.g., a smartphone), a computer device, a portable multimedia device, a portable medical device, a camera, a wearable device, or a home appliance. According to an embodiment of the disclosure, the electronic devices are not limited to those described above.

It should be appreciated that various embodiments of the present disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include any one of, or all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), it means that the element may be coupled with the other element directly (e.g., wiredly), wirelessly, or via a third element.

As used herein, the term "module" may include a unit implemented in hardware, software, or firmware, and may interchangeably be used with other terms, for example, "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC).

Various embodiments as set forth herein may be implemented as software (e.g., the program 140) including one or more instructions that are stored in a storage medium (e.g., internal memory 136 or external memory 138) that is readable by a machine (e.g., the first electronic device 101). For example, a processor (e.g., the processor 120) of the machine (e.g., the first electronic device 101) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a compiler or a code executable by an interpreter. The machine-readable storage medium may be provided in the form of a non-transitory storage medium. Wherein, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment, a method according to various embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., PlayStore™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments, each component (e.g., a module or a program) of the above-described components may include a single entity or multiple entities. According to various embodiments, one or more of the above-described components may be omitted, or one or more other components may be added. Alternatively or additionally, a plurality of components (e.g., modules or programs) may be integrated into a single component. In such a case, according to various embodiments, the integrated component may still perform one or more functions of each of the plurality of components in the same or similar manner as they are performed by a corresponding one of the plurality of components before the integration. According to various embodiments, operations performed by the module, the program, or another component may be carried out sequentially, in parallel, repeatedly, or heuristically, or one or more of the operations may be executed in a different order or omitted, or one or more other operations may be added.

Figure 2:
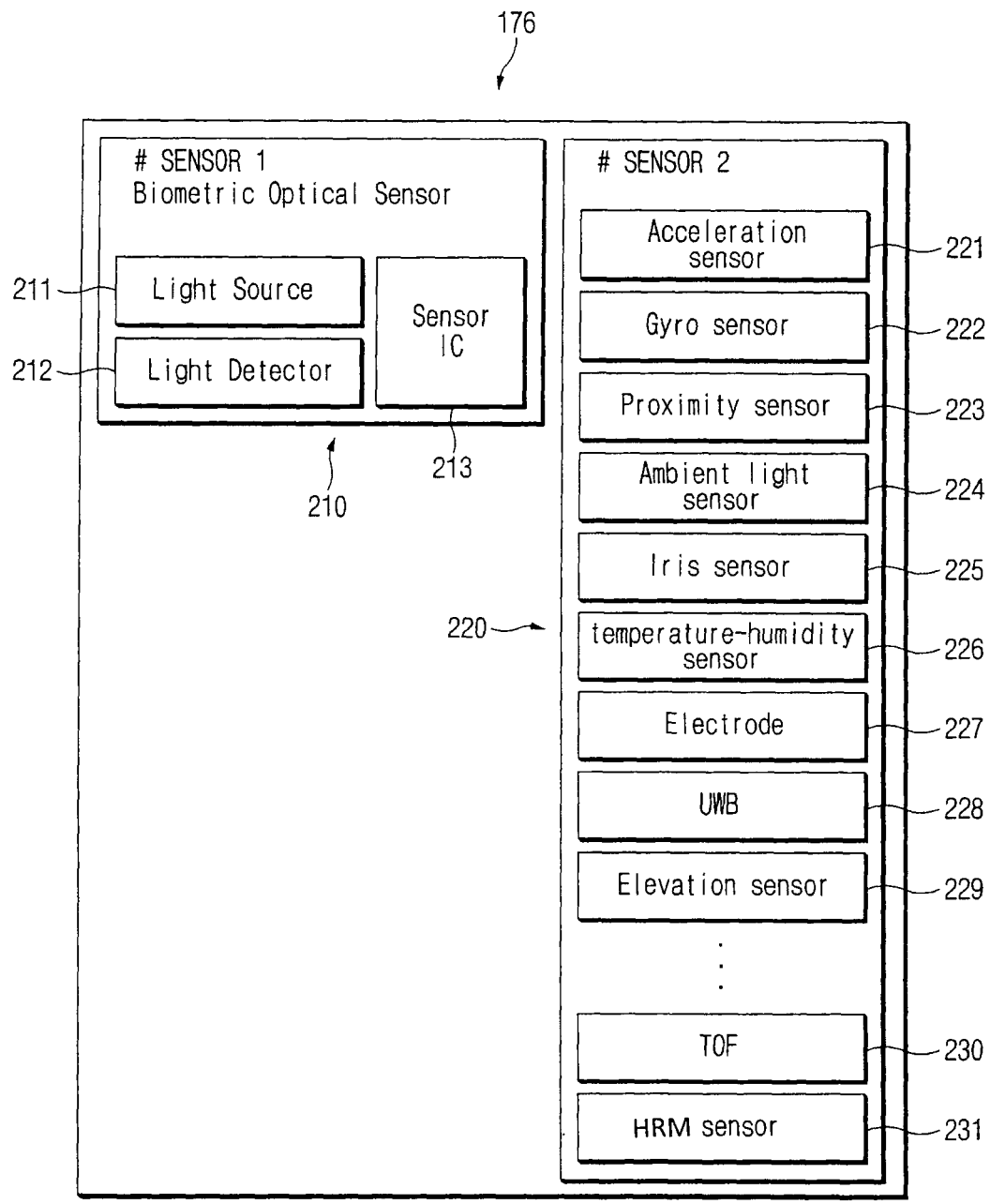
FIG. 2 is a block diagram of a sensor module of the electronic device of FIG. 1.

FIG. 2 is a block diagram of a sensor module 176 of the first electronic device 101 of FIG. 1. Referring to FIG. 2, the sensor module 176 may include a first sensor module 210 and a second sensor module 220.

The first sensor module 210 may be a biometric optical sensor. The first sensor module 210 may include a light source 211, a light detector 212 and a senor integrated circuit (IC) 213.

The light source 211 may include at least one LED emitting light at N number of wavelengths. The light source 211 may include an emitter that emits in the green wavelength band. The green wavelength band may be the wavelength band most commonly used to measure heart rate, because green light may achieve relatively shallow penetration of the skin while being robust against noise. The light source 211 may include an emitter that emits in the red wavelength band. The red wavelength band may penetrate relatively deeply into the skin and thus may be used to measure more accurately the heart rate. The light source 211 may include an emitter than emits in the infrared wavelength band. In addition to the red wavelength band, the infrared wavelength band may be used to obtain more biometric information such as the heart rate and in-blood oxygen saturation $SpO_2$. The red, green and infrared wavelengths may be used to obtain skin tone measurement. The light source 211 may include an emitter that emits in the blue wavelength band. The blue wavelength band may be used to measure blood glucose. As the light source 211 includes emitters of various wavelength bands, various biometric information may be acquired. For each wavelength band, for example the green band, the light source 211 may include multiple emitters.

The light detector 212 may include at least one photodiode. The light detector 212 may have a plurality of photodiodes arranged and spaced apart from each other by a predetermined equal spacing or by different distances. The light detector 212 may be used to detect light which is emitted from the light source 211 and then reflected by the user's skin.

The senor integrated circuit 213 may include a sensor driver controller to directly control the sensor 210, and may further include an analog-to-digital converter. The sensor driver controller may include an emitter controller and a detector controller. The emitter controller may directly drive the light source 211 or a component such as an emitter included in the light source 211. The detector controller may directly drive the light detector 212 or a component included in light detector 212, such as a photodiode.

The sensor driver controller may include an analog front end. The sensor driver controller or the analog front end may include at least one of an LED driver, an amplifier that amplifies a value of the detector, an analog-to-digital converter that converts an analog value from the detector to a digital value, or a controller that controls the LED driver and the analog-to-digital converter.

Signal in the light incoming through the light detector 212 may be transmitted to a processor after it is passed through a variety of filters and the analog-to-digital converter. A value corresponding to the light may be extracted as biometric information value to be processed using an algorithm and may be displayed to the user, stored in a related application or transmitted to another device.

The second sensor module 220 may include at least one of following sensors.

The second sensor module 220 may include an acceleration sensor 221, a gyro sensor 222, a proximity sensor 223, an iris sensor 225, a heart rate monitor (HRM) sensor 231, and a body temperature sensor to determine a state of the user.

The second sensor module 220 may further include a temperature-humidity sensor 226, an ambient light sensor 224, an UWB (Ultra-wideband) sensor 228, an elevation sensor 229, or a TOF (Time of flight) sensor 230 for determining an external environment of the user.

The second sensor module 220 may include additional biometric sensors. For example, in addition to the optical biometric sensor of the first sensor module 210, the second sensor module 220 may include an electrode 227 which may measure at least one of electrocardiogram (ECG), galvanic skin response (GSR), electroencephalography (EEG), or bioelectrical impedance analysis (BIA).

In addition to the sensor shown in FIG. 2, a gas sensor, a fine dust sensor may be further included in the sensor module.

In FIG. 2, the sensor module 176 is divided into the first sensor module 210 and the second sensor module 220. In another example, sensors included in the first sensor module 210 and the second sensor module 220 may be connected to the senor integrated circuit 213.

At least one of the plurality of sensors included in the sensor module 176 of FIG. 2 may be omitted.

Hereinafter, with reference to FIG. 3A to FIG. 3C, the structure of the electronic device according to an embodiment it will be described.

Figure 3A:
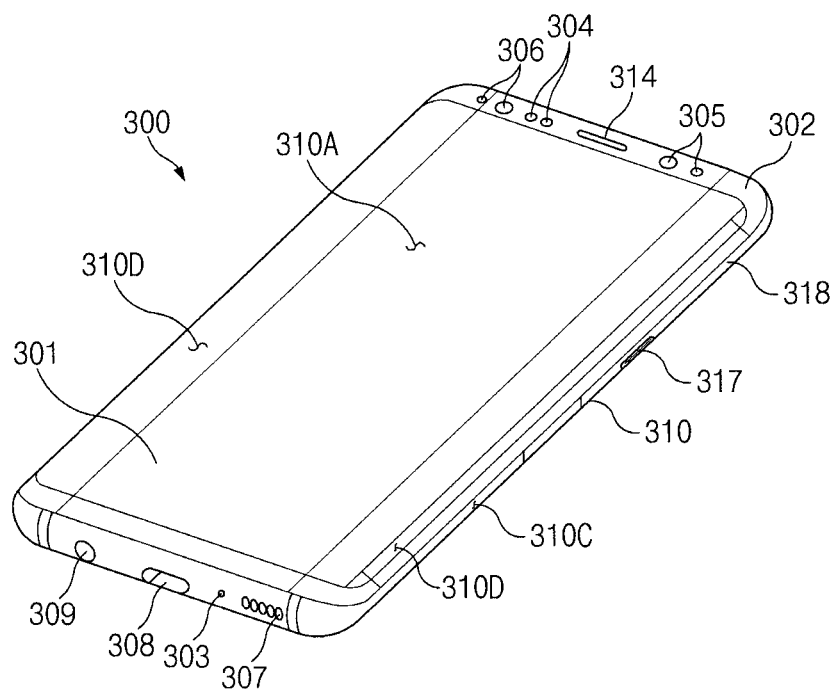
FIG. 3A is a perspective view of a front face of an electronic device according to an embodiment.

FIG. 3A is a perspective view of a front surface of the electronic device according to an embodiment. FIG. 3B is a perspective view of a rear surface of the electronic device of FIG. 3A. FIG. 3C is an exploded perspective view of the electronic device of FIG. 3A.

Figure 3B:
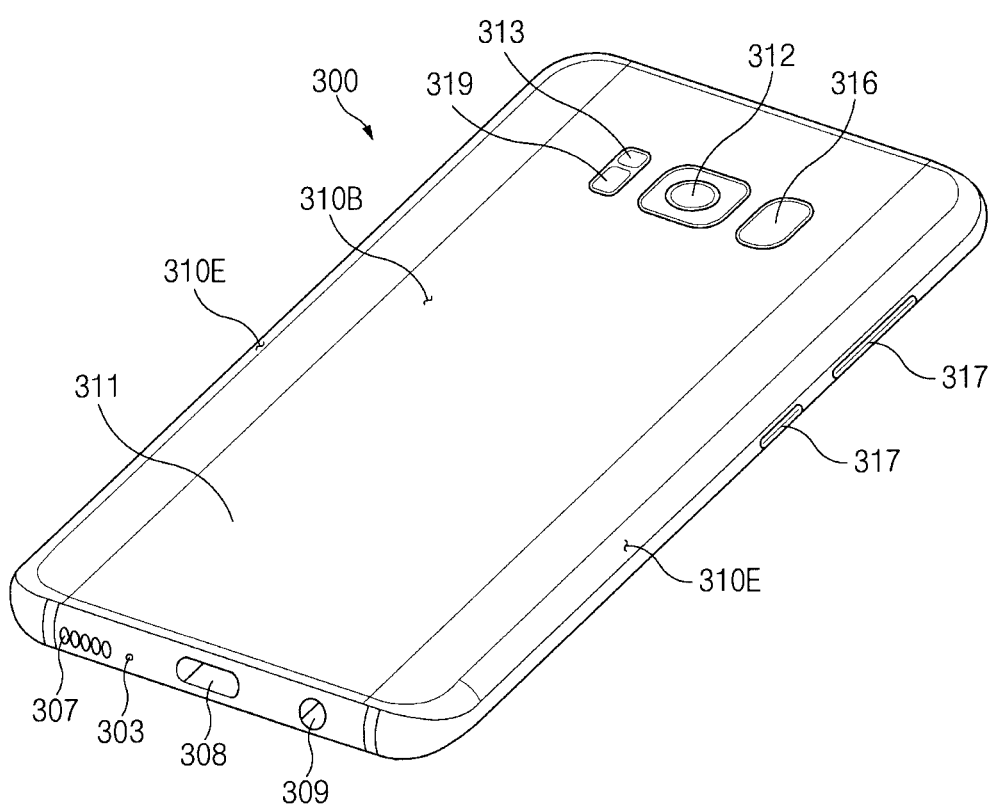
FIG. 3B is a perspective view of a rear face of the electronic device of FIG. 3A.

Referring to FIG. 3A and FIG. 3B, an electronic device 300 according to an embodiment may include a housing 310 including a first surface or front surface 310A, a second surface or rear surface 310B, and a side surface 310C surrounding a space between the first surface 310A and the second surface 310B. In another embodiment (not shown), the housing may refer to a structure that partially forms the first surface 310A, the second surface 310B, and the side surface 310C of FIG. 1. According to one embodiment, the first surface 310A may be formed by a front plate 302 (e.g., a glass plate, or a polymer plate including various coating layers) that is at least partially substantially transparent. The second surface 310B may be formed by a substantially opaque rear plate 311. The rear plate 311 may be made of, for example, a coated or colored glass, ceramic, polymer, a metal such as aluminum, stainless steel (STS), or magnesium, or a combination of at least two of the above materials. The side surface 310C may be combined with the front plate 302 and rear plate 311 and may be formed of a side bezel structure or "side member" 318 including metal and/or polymer. In some embodiments, the rear plate 311 and the side bezel structure 318 may be integrally formed with each other and include the same material such as a metal material such as aluminum.

In the illustrated embodiment, the front plate 302 includes two first regions 310D bending from the first surface 310A toward the rear plate 311. Each first region 310D extends seamlessly along each long side of the front plate 302. In the illustrated embodiment (FIG. 2), the rear plate 311 may include two second regions 310E bending from the second surface 310B toward the front plate 302. Each second region 310B extends seamlessly across each long side of the rear plate 311. In some embodiments, the front plate 302 or the rear plate 311 may include only one of the first regions 310D or only one of the second regions 310E. In another embodiment, a portion of the first region 310D or a portion of the second region 310E may not be included. In the embodiments, when viewed from a side of the electronic device 300, the side bezel structure 318 has a first thickness or width on a side where the first regions 310D or the second regions 310E are not located, and a second thickness smaller than the first thickness on a side where the first regions 310D or second regions 310E are located.

According to one embodiment, the electronic device 300 may include at least one of a display 301, audio modules 303, 307 and 314, sensor modules 304, 316 and 319, camera modules 305, 312 and 313, a key input device 317, a light-emitting element 306, or connector holes 308 and 309. In some embodiments, the electronic device 300 may be free of at least one of the components, for example, the key input device 317, or the light-emitting element 306, or may additionally include other components.

The display 301 may be exposed through, for example, a substantial portion of the front plate 302. In some embodiments, at least a portion of the display 301 may be exposed through the front plate 302 forming the first surface 310A and the first region 310D of the side surface 310C. In some embodiments, an edge of the display 301 may be formed in substantially the same shape as a shape of an adjacent outline of the front plate 302. In another embodiment (not shown), in order to expand an area where the display 301 is exposed, a distance between an outside of the display 301 and an outside of the front plate 302 may be substantially uniform.

In another embodiment (not shown), a recess or opening may be defined in a portion of a screen display region of the display 301. The electronic device 300 may include at least one of the audio module 314, the sensor module 304, the camera module 305, and the light-emitting element 306 aligned with the recess or the opening. In another embodiment (not shown), the electronic device 300 may include at least one of the audio module 314, the sensor module 304, the camera module 305, the fingerprint sensor 316, and the light-emitting element 306 on a back surface of the screen display region of display 301. In another embodiment (not shown), the display 301 may be coupled with or may be adjacent to a touch sensing circuit, a pressure sensor that may measure an intensity (pressure) of a touch, and/or a digitizer that detects a magnetic field based stylus pen. In some embodiments, at least a portion of the sensor module 304 and 319, and/or at least a portion of the key input device 317 may be disposed in the first regions 310D and/or the second regions 310E.

The audio module 303, 307 and 314 may include the microphone hole 303 and the speaker holes 307 and 314. In the microphone hole 303, a microphone may be disposed therein for acquiring an external sound. In some embodiments, a plurality of microphones may be arranged to sense a direction of the sound. The speaker holes 307 and 314 may include the external speaker hole 307 and the call receiver hole 314. In some embodiments, the speaker holes 307 and 314 and microphone hole 303 may be combined into a single hole, or the speaker may be included without the speaker holes 307 and 314 (for example, piezo speaker).

The sensor modules 304, 316 and 319 may generate an electrical signal or data value corresponding to an internal operating state of the electronic device 300 or an external environmental state thereto. The sensor modules 304, 316, and 319 may include, for example, the first sensor module 304 (e.g. proximity sensor) and/or a second sensor module (not shown) (e.g. fingerprint sensor) disposed on the first surface 310A of the housing 310, and/or the third sensor module 319 (e.g., HRM sensor) and/or the fourth sensor module 316 (e.g., fingerprint sensor) disposed on the second surface 310B of the housing 310. The fingerprint sensor may be placed on the second surface 310B as well as the first surface 310A (e.g., display 301) of the housing 310. The electronic device 300 may further include a sensor module not shown, for example, at least one of a gesture sensor, a gyro sensor, a barometric pressure sensor, a magnetic sensor, an acceleration sensor, a grip sensor, a color sensor, an IR (infrared) sensor, a biometric sensor, a temperature sensor, a humidity sensor, or an illuminance sensor.

The camera modules 305, 312, and 313 may include the first camera device 305 disposed on the first surface 310A of the electronic device 300, the second camera device 312 disposed on the second surface 310B, and/or the flash 313 disposed on the second surface 310B. Each of the camera devices 305 and 312 may include one or a plurality of lenses, an image sensor, and/or an image signal processor. The flash 313 may include, for example, a light emitting diode or a xenon ramp. In some embodiments, two or more lenses (an infrared camera, wide angle and telephoto lenses), and image sensors may be disposed on one surface of the electronic device 300.

The key input device 317 may be disposed on the side surface 310C of the housing 310. In another embodiment, the electronic device 300 may not include an entirety or a portion of the mentioned key input device 317. In this connection, the portion of the key input device 317 not included therein may be implemented in a different form such as a soft key on the display 301. In some embodiments, the key input device may include the sensor module 316 disposed on the second surface 310B of the housing 310.

The light-emitting element 306 may be disposed, for example, on the first surface 310A of the housing 310. The light-emitting element 306 may, for example, provide state information of the electronic device 300 optically. In another embodiment, the light-emitting element 306 may, for example, provide a light source that is associated with an operation of the camera module 305. The light-emitting element 306 may include, for example, an LED, an IR LED, and a xenon ramp.

The connector holes 308 and 309 may include the first connector hole 308 configured for accommodating a connector (e.g., USB connector) for transmitting and receiving power and/or data with an external electronic device, and/or a second connector hole 309, for example, an earphone jack, which may accommodate a connector for transmitting and receiving an audio signal with an external electronic device.

Figure 3C:
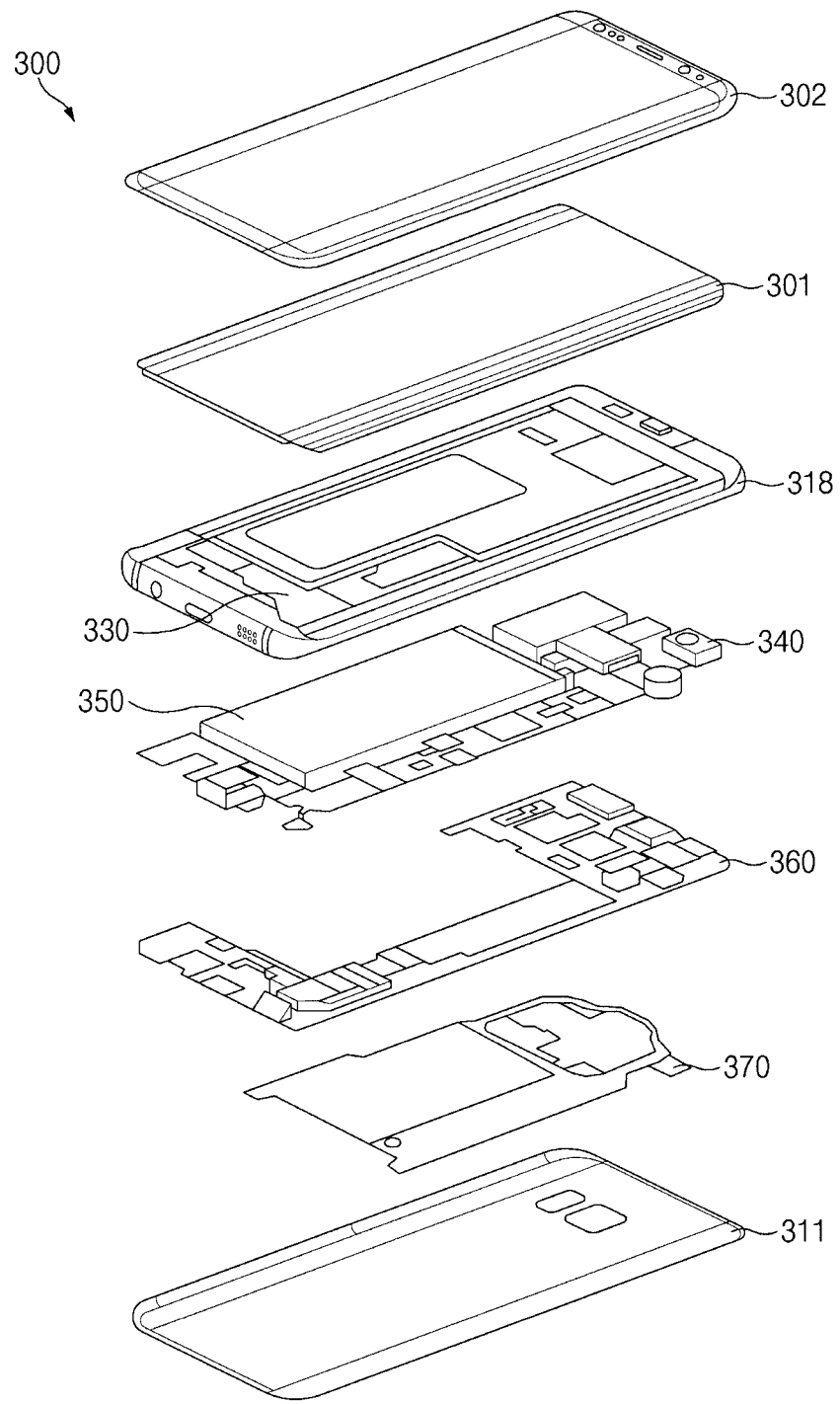
FIG. 3C is an exploded perspective view of the electronic device of FIG. 3A.

Referring to FIG. 3C, the electronic device 300 may include the side bezel structure 318, a first support member 330 (e.g. bracket), the front plate 302, the display 301, a printed circuit board 340, a battery 350, a second support member 360 (e.g. rear case), an antenna 370, and the rear plate 311. In some embodiments, the electronic device 300 may be free of at least one of the components, for example, the first support member 330, or the second support member 360, or may additionally include other components. At least one of the components of the electronic device 300 may be the same as or similar to at least one of the components of the electronic device 101 of FIG. 1, or FIG. 2. Thus, duplicate descriptions thereof will be omitted below.

The first support member 330 may be disposed inside the electronic device 300 and may be connected with the side bezel structure 318 or may be integrally formed with the side bezel structure 318. The first support member 330 may be made of, for example, a metallic material and/or a nonmetallic material (polymer) such as a polymer material. The first support member 330 may have one surface coupled to the display 301 and the other surface coupled to the printed circuit board 340. On the printed circuit board 340, a processor, a memory, and/or an interface may be mounted. The processor may include, for example, one or more of a central processing unit, an application processor, a graphics processing unit, an image signal processor, a sensor hub processor, or a communication processor. The processor may include a microprocessor or any suitable type of processing circuitry, such as one or more general-purpose processors (e.g., ARM-based processors), a Digital Signal Processor (DSP), a Programmable Logic Device (PLD), an Application-Specific Integrated Circuit (ASIC), a Field-Programmable Gate Array (FPGA), a Graphical Processing Unit (GPU), a video card controller, etc. In addition, it would be recognized that when a general purpose computer accesses code for implementing the processing shown herein, the execution of the code transforms the general purpose computer into a special purpose computer for executing the processing shown herein. Certain of the functions and steps provided in the Figures may be implemented in hardware, software or a combination of both and may be performed in whole or in part within the programmed instructions of a computer. No claim element herein is to be construed under the provisions of 35 U.S.C. § 112(f), unless the element is expressly recited using the phrase "means for." In addition, an artisan understands and appreciates that a "processor" or "microprocessor" may be hardware in the claimed disclosure. Under the broadest reasonable interpretation, the appended claims are statutory subject matter in compliance with 35 U.S.C. § 101.

The memory may include, for example, a volatile memory or a nonvolatile memory.

The interface may include, for example, an HDMI (high definition multimedia interface), a USB (universal serial bus) interface, an SD card interface, and/or an audio interface. The interface may, for example, electrically or physically connect the electronic device 300 to an external electronic device. The interface may include an USB connector, a SD card/MMC connector, or an audio connector.

The battery 350 refers to a device for powering at least one component of the electronic device 300, and may include, for example, a non-rechargeable primary cell, or a rechargeable secondary cell, or a fuel cell. At least a portion of the battery 350 may be substantially coplanar with, for example, the printed circuit board 340. The battery 350 may be integrally with and disposed inside the electronic device 300 or may be detachable from the electronic device 300.

The antenna 370 may be disposed between the rear plate 311 and the battery 350. The antenna 370 may include, for example, an NFC (near field communication) antenna, a wireless charging antenna, and/or an MST (magnetic secure transmission) antenna. The antenna 370 may, for example, perform short-range communication with an external device or wirelessly transmit and receive power required for charging the electronic device 300. In another embodiment, an antenna structure may be formed of a portion of the side bezel structure 318 and/or the first support member 330 or a combination thereof.

Hereinafter, referring to FIG. 4 and FIG. 5, an operation method of the electronic device according to an embodiment will be described.

Figure 4:
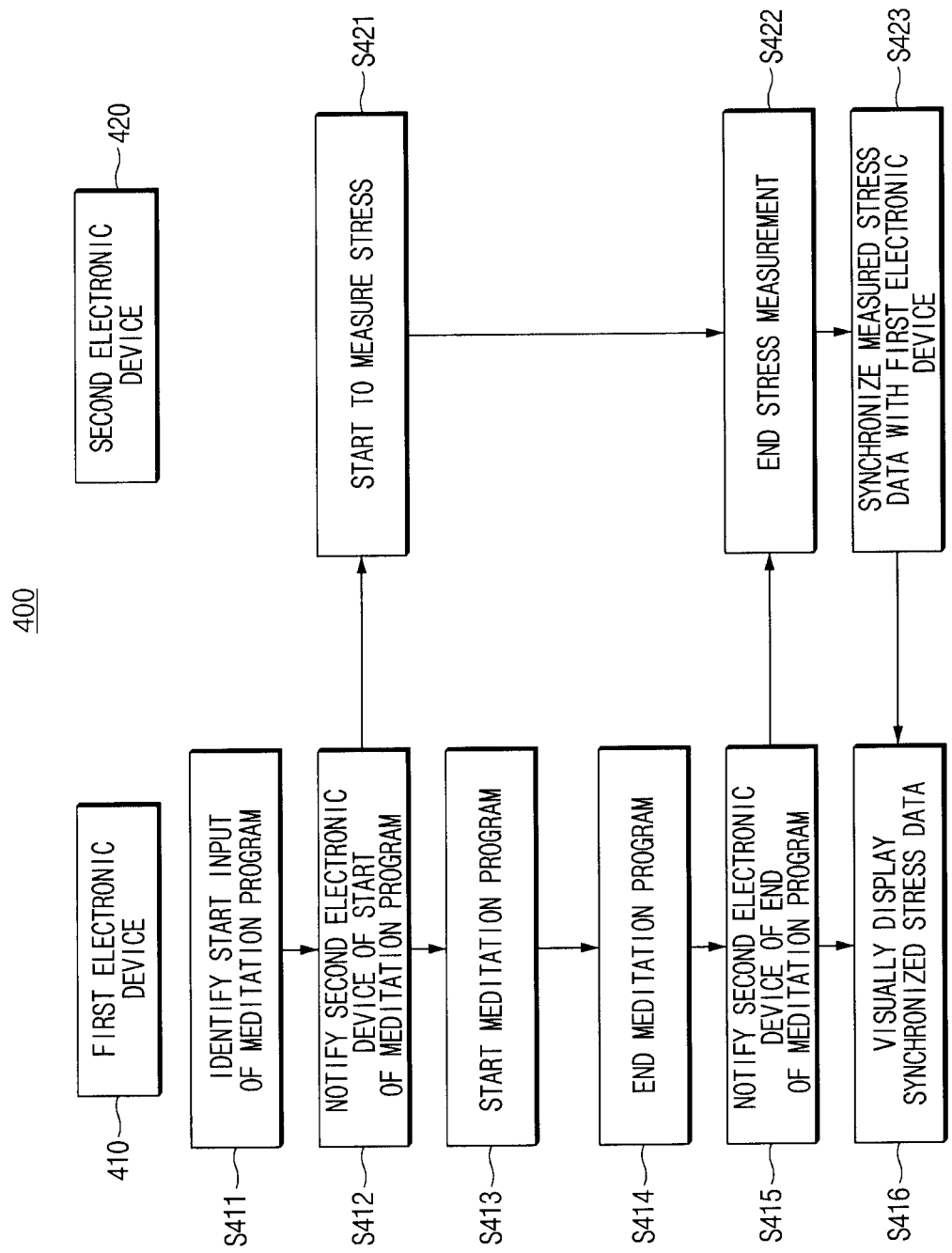
FIG. 4 is a flow chart showing an operation method of an electronic device according to an embodiment.

FIG. 4 is a flow chart 400 showing the operation method of the electronic device according to an embodiment. FIG. 5 is a diagram 500 showing a user interface of the electronic device according to an embodiment in the sequence of operation disclosed in FIG. 4.

Figure 5:
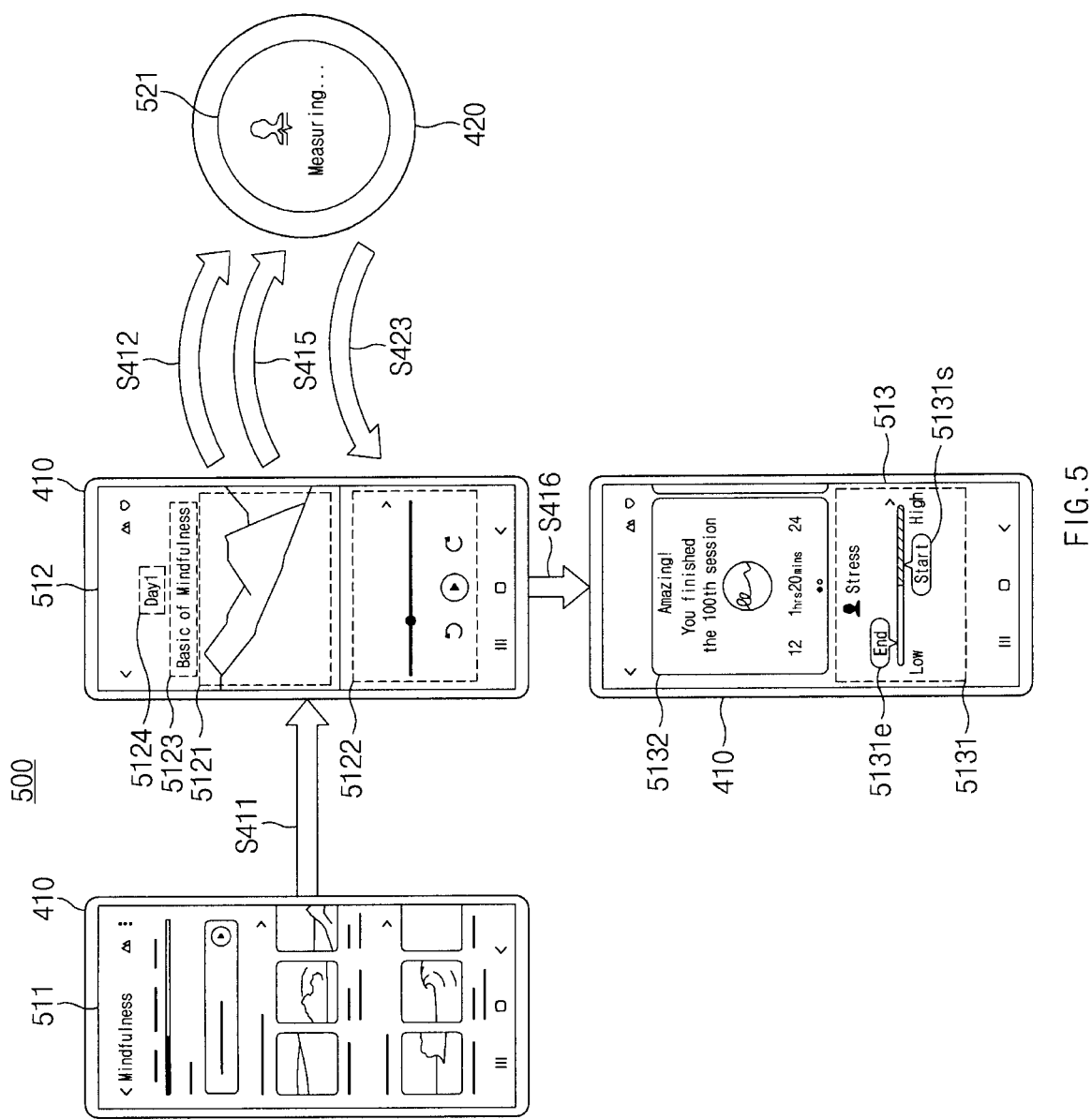
FIG. 5 is a diagram showing a user interface, shown in relation to a sequence of operations, of an electronic device according to one embodiment.

Referring to FIG. 4 and FIG. 5, a first electronic device 410 (e.g., the electronic device 101 of FIG. 1 or the electronic device 300 of FIG. 3A) may identify a user's start input of a meditation program (S411). The first electronic device 410 may include a meditation application. Herein, the term "meditation application" may refer to the computer application related to meditation, while "meditation program" may be a specific routine for meditation that is included in the meditation application. The first electronic device 410 may download or update the meditation program from a server (e.g., the server 108 in FIG. 1). Alternatively, the meditation application may be embedded or stored in the first electronic device 410.

The first electronic device 410 may display one or more meditation programs included in the meditation application and may provide a first user interface 511 that may receive the start input of the meditation program from the user. The user may select a desired meditation program on the first user interface 511 of the first electronic device 410, and may input the start of the desired meditation program. The start input of the meditation program may be embodied as touching of the meditation program displayed on the first user interface 511. The first electronic device 410 may receive the start input of the meditation program selected by the user via the first user interface 511.

After identifying the start input of the meditation program, the first electronic device 410 may provide a second user interface 512 to display contents of the meditation program. The second user interface 512 may include at least one of information about the meditation program, such as meditation screen 5121, interface 5122 for controlling meditation music, title 5123 of the meditation program, and meditation program execution count 5124.

When the first electronic device 410 identifies the start input of the meditation program, the first electronic device 410 may transmit a start notification of the meditation program to a second electronic device 420 (e.g., the first or second wearable electronic device 102 or 104 in FIG. 1) (S412). The start notification of the meditation program may include a stress measurement start command. Further, when the first electronic device 410 identifies the start input of the meditation program, the first electronic device 410 may start the meditation program (S413). The start notification operation S412 of the meditation program and the start operation S413 of the meditation program may be reversed in order, or alternatively, may be executed simultaneously.

In FIG. 5, it is shown that receiving the start input of the meditation program selected by the user is carried out on the first user interface 511 of the first electronic device 410. But the disclosure is not so limited. When the second electronic device 420 includes a user interface that may receive the start input of the meditation program, the second electronic device 420 may receive the start input and transmit the same to the first electronic device 410, and then the first electronic device 410 may start the meditation program according to the start input received from the second electronic device 420 and then provide the second user interface 512. In this case, operation S412 informing the second electronic device 420 of the start of the meditation program may be omitted.

The second electronic device 420 may be an electronic device that may continuously measure the stress level of the user of the second electronic device 420. The second electronic device 420 may perform the stress measurement by at least one sensor included in the sensor module 176 of FIG. 2. The second electronic device 420 may be a wearable device and may be an electronic device that may continuously measure the stress level of the user of the second electronic device 420. The second electronic device 420 may be an electronic device capable of wired or wireless communication with the first electronic device 410, for example via short-range or long-range communication with the first electronic device 410. The second electronic device 420 may be one of the external electronic devices 102 and 104 of FIG. 1. An embodiment of the second electronic device 420 will be described later in FIG. 10.

When identifying the start notification of the meditation program, the second electronic device 420 may start the user's stress measurement for the meditation program at S421. In connection to this operation, the user's stress measurement for the meditation program may refer to continuously measuring the stress during the execution of the meditation program. To continuously measure the stress, for example, measurements may be performed every X number of milliseconds (ms) or microseconds (μs). This measurement period may not be perceived by a person.

When the second electronic device 420 identifies the start notification of the meditation program, and when an always-stress measurement mode is set, the second electronic device 420 may change the always-stress measurement mode to a mode of measuring the stress continuously as described above, and may start the user's stress measurement for the meditation program in the changed mode. In this connection, the always-stress measurement mode may refer to a mode in which the device measures the stress of the user at all times, regardless of the execution of the meditation program. For example, in the always-stress measurement mode, the second electronic device 420 may measure stress every few seconds, every few minutes, every few hours, or at the same time every day. When it is determined that a stress measurement period set in the second electronic device 420 when the meditation program start notification is received is suitable for the user's stress measurement for the meditation program, the above-described operation to change the measurement period may be omitted. The second electronic device 420 may continue to measure the user stress level at the set measurement period.

Alternatively, when the second electronic device 420 identifies the start notification of the meditation program, and when the always-stress measurement mode is not set in the second electronic device 420, the second electronic device 420 may set the above-described period or the mode of continuously measuring the stress and then may start the stress measurement of the user for the meditation program. The stress of the user may be measured by a biometric optical sensor included in the second electronic device 420. Because the stress of the user is continuously measured during the execution of the meditation program, the stress change of the user according to the meditation program may be recorded in real time. The second electronic device 420 may display a fourth user interface 521 indicating that the stress is being measured.

When the first electronic device 410 identifies an ending input of the user, the first electronic device 410 may end the meditation program (S414). When the first electronic device 410 identifies the user's meditation program ending input, the first electronic device 410 may transmit the ending notification of the meditation program to the second electronic device 420. The meditation program ending notification may include a stress measurement ending command. The ending operation S414 and the ending notification transmission operation S415 of the meditation program may be reversed in order or may be executed simultaneously.

The meditation program ending input of the user may be received via the second user interface 512 of the first electronic device 410. Alternatively, when the second electronic device 420 includes a user interface that may receive the ending input of the meditation program, the meditation program ending input of the user may be received via the second electronic device 420. In this case, the second electronic device 420 may receive the ending input from the user and transmit the same to the first electronic device 410. Then, the first electronic device 410 may end the meditation program according to the ending input as received from the second electronic device 420. In this case, operation S415 of informing the second electronic device 420 of the ending of the meditation program may be omitted.

When the second electronic device 420 identifies the ending notification of the meditation program, the second electronic device 420 may end the user's stress measurement for the meditation program (S422). In the case where an always-stress measurement mode was set when the second electronic device 420 identified the start notification of the meditation program, when the second electronic device 420 identifies the ending notification of the meditation program, the second electronic device 420 may switch the stress measurement mode from the user stress measurement for meditation program back to the always-stress measurement mode. The second electronic device 420 may synchronize stress data measured during the execution of the meditation program with the first electronic device 410 (S423). When the measurement period for the user's stress measurement for the meditation program and the measurement period for the always-stress measurement are equal to each other, the second electronic device 420 may transmit the measured stress data from the start to the end of the meditation program to the first electronic device 410 without changing setting for the stress measurement.

The first electronic device 410 may receive the measured stress data from the second electronic device 420. The first electronic device 410 may display the received stress data (S416). The first electronic device 410 may provide a third user interface 513 including visual information 5131 that visually indicates the result from measuring the user's stress change while the meditation program is executed. The first electronic device 410 may present, to the user, the visual information 5131 which compares the stress level at the start 5131s and the stress level at the end 5131e of the meditation program, on the third user interface 513. The stress change of the user measured while the meditation program is executed may be displayed as a numerical value. In another example, as shown in the visual information 5131 of FIG. 5, the stress change may be indicated intuitively. For example, increase in stress may be shown as a transition from blue to red. The third user interface 513 may use the visual information 5131 to indicate to the user whether stress is reduced using the meditation program. FIG. 5 shows an example of the visual information 5131. The visual information 5131 may indicate the user's stress value in various visual forms such as graphs, shapes, images, colors, graphics, scores, or levels or combinations thereof.

Further, the third user interface 513 may include information about the meditation program, such as the meditation program title, the meditation program type, and the meditation program execution time.

Further, the first electronic device 410 may store therein information about the meditation program that was previously executed by the user. According to an embodiment, based on the information about the meditation programs previously executed by the user, the first electronic device 410 may display, on the third user interface 513, information 5132 reflecting the meditation program execution record of the user, such as a meditation program execution count, a meditation program continuous execution count, a writing to compliment the meditation program execution, a writing to inspire the meditation program execution.

Further, according to one embodiment, the third user interface 513 may include biometric information such as blood pressure and heart rate.

In FIG. 4, it is shown that after the stress measurement is completed, the second electronic device 420 synchronizes the measured stress data with the first electronic device 410 (S423). The disclosure is not so limited. According to another embodiment, the stress data measured in the second electronic device 420 may be synchronized, in real time, with the first electronic device 410. Further, according to another embodiment, the first electronic device 410 may display the stress data synchronized in real time to the user in real time.

According to an embodiment, when the first electronic device 410 is an electronic device that may continuously measure the stress of the user, all of the above-described operations executed in the second electronic device 420 may be executed in the first electronic device 410.

The order of the operations of the flowchart 400 shown in FIG. 4 may be changed according to other embodiments, as explained above. Also as explained above, some operations thereof may be omitted.

Hereinafter, with reference to FIG. 6 and FIG. 7, an operation method of the electronic device according to an embodiment will be described. Descriptions of the same configuration and operation as in the above-described embodiment may be omitted.

Figure 6:
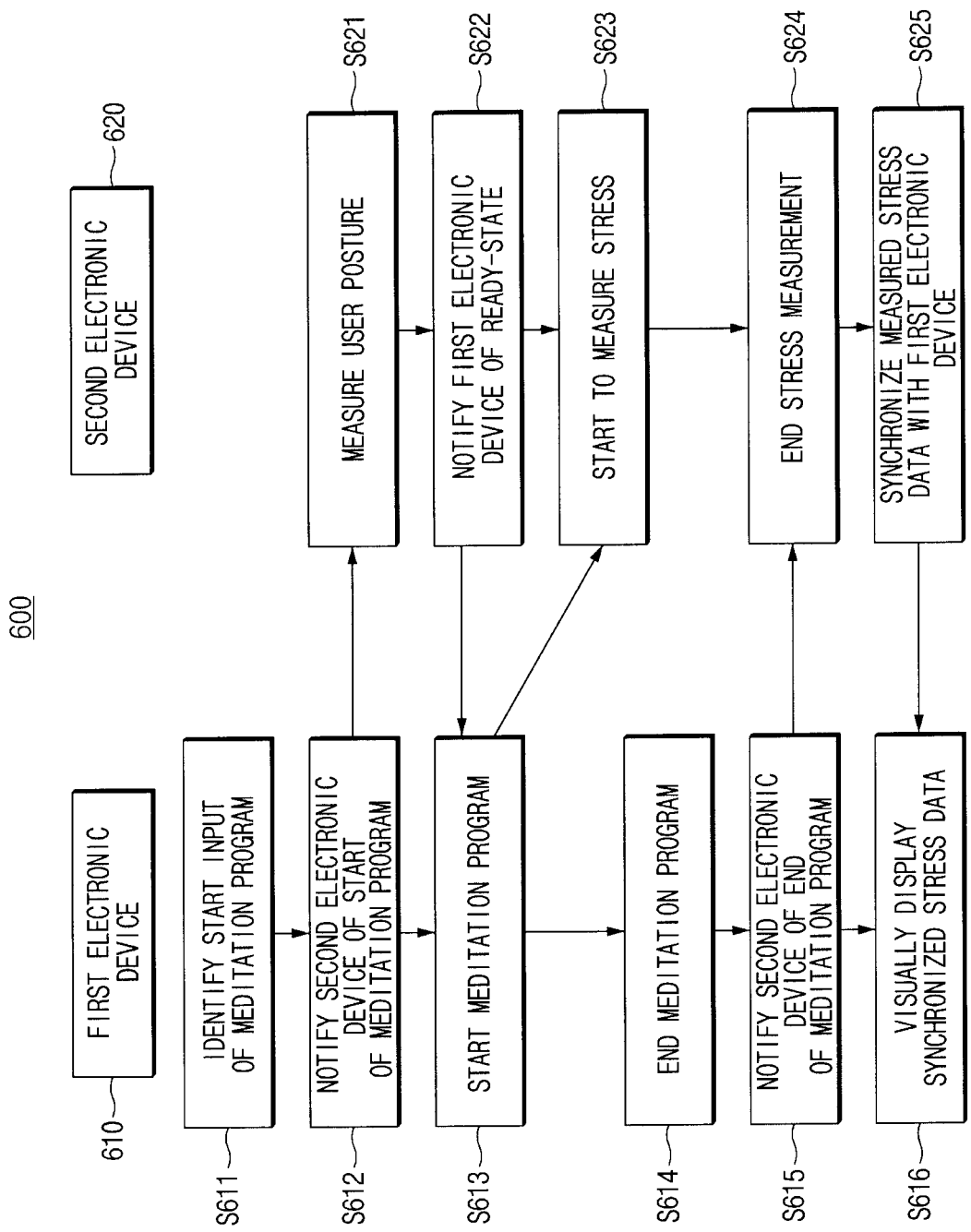
FIG. 6 is a flow chart showing an operation method of an electronic device according to an embodiment.

FIG. 6 is a flow chart 600 showing an operation method of the electronic device according to an embodiment. FIG. 7 is a diagram illustrating a user interface of an electronic device according to one embodiment in a sequence of operations as disclosed in FIG. 6.

Figure 7:
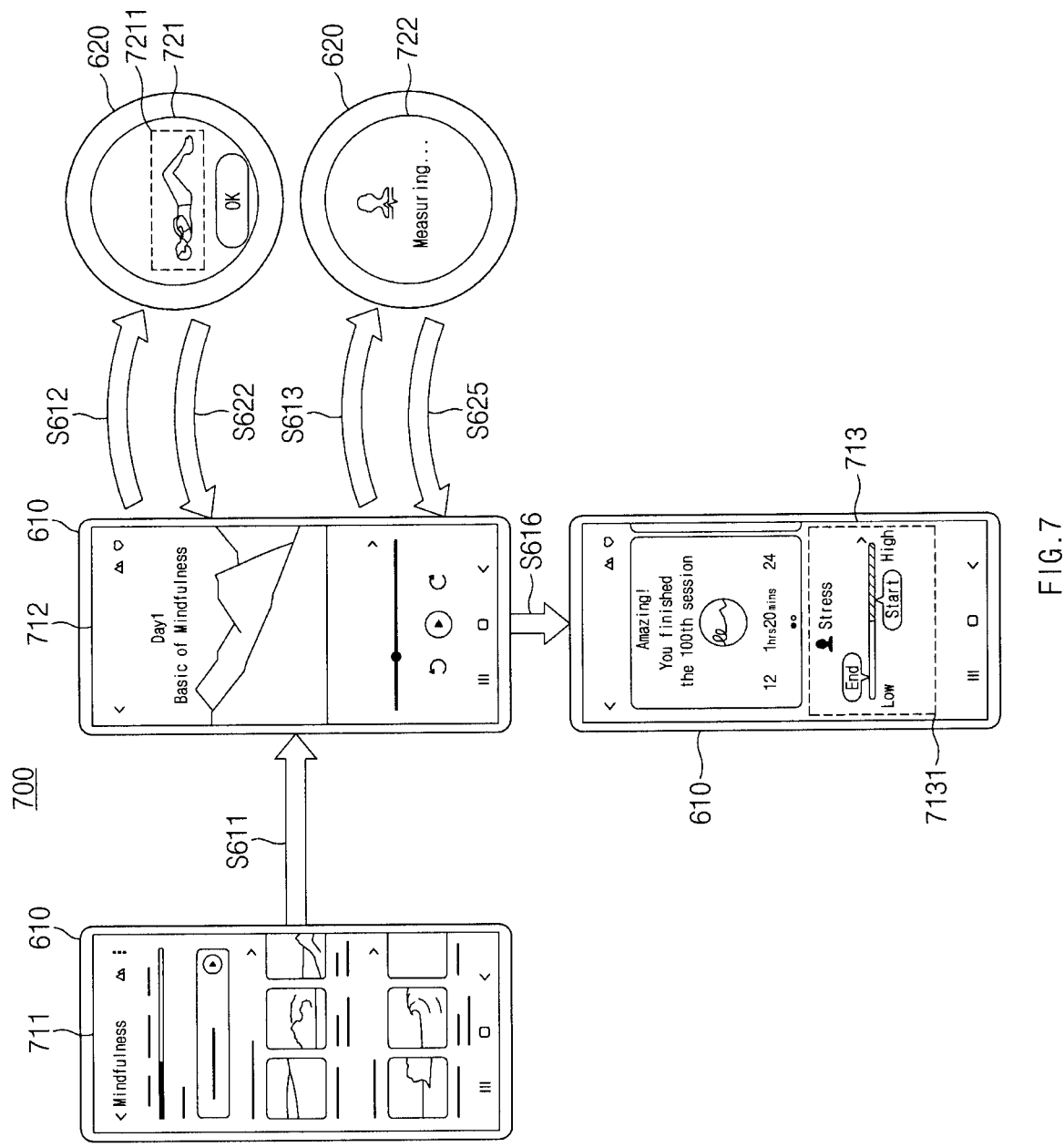
FIG. 7 is a view showing a user interface, shown in relation to a sequence of operations, of an electronic device according to one embodiment.

Referring to FIG. 6 and FIG. 7, a first electronic device 610 (e.g., the electronic device 101 of FIG. 1, the electronic device 300 of FIG. 3A, or the first electronic device 410 of FIG. 4) may identify the user's start input of the meditation program S611. The start input of the meditation program may be received via a first user interface 711 of the first electronic device 610. Alternatively, when a second electronic device 620 (e.g., the first or second wearable electronic device 102 or 104 of FIG. 1 or second electronic device 420 of FIG. 4) includes a user interface that may receive the start input of the meditation program, the start input may be received via the user interface of the second electronic device 620.

When the first electronic device 610 identifies the start input of the meditation program, the first electronic device 610 may transmit the start notification of the meditation program to the second electronic device 620. When the start input of the meditation program is received by the second electronic device 620, the start notification transmission operation S612 may be omitted.

When identifying the start notification of the meditation program, the second electronic device 620 may start posture measurement of the user (S621). The posture of the user may be measured by a motion sensor (e.g., an acceleration sensor (e.g., the acceleration sensor 221 of FIG. 2)) and/or a gyro sensor (e.g., the gyro sensor 222 of FIG. 2)) included in the second electronic device 620. Alternatively, whether the posture of the user is stable may be determined based on measurement of heart rate stability of the user using a heart rate sensor (the first sensor module 210 and/or the heart rate sensor 231 of FIG. 2). The second electronic device 620 may identify, based on at least some of the data measured by the motion sensor, heart rate sensor, or a combination thereof, whether the posture of the user is suitable for meditation. Stationary and stable postures may be suitable for meditation. According to an embodiment, the second electronic device 620 may display a fourth user interface 721 displaying guide information 7211 guiding a posture for meditation. The guide information 7211 may include one or more meditation postures such as lotus position, standing posture, lying down posture, posture where hands are placed on the chest, or a sitting posture where hands touch knees.

When the second electronic device 620 identifies that the user has taken the posture suitable for meditation, the second electronic device 620 may send a ready-to-start notification to the first electronic device 610 (S622). For example, when the second electronic device 620 identifies, based on at least some of the data measured by the motion sensor, heart rate sensor or a combination thereof, that the user has taken a posture suitable for meditation, the second electronic device 620 may send a ready-to-start notification to the first electronic device 610. Alternatively, when the second electronic device 620 receives an input indicating that the user is ready for meditation from the user via the fourth user interface 721, the second electronic device 620 may send a ready-to-start notification to the first electronic device 610. The ready-to-start user input may correspond to touching of an OK button on the fourth user interface 721.

When the first electronic device 610 receives the ready-to-start notification from the second electronic device 620, the first electronic device 610 may start the meditation program (S613). The first electronic device 610 may provide a second user interface 712 that displays the meditation program for the start of the meditation program.

When the second electronic device 620 receives a notification indicating that the meditation program has been started from the first electronic device 610, the second electronic device 620 may start the user's stress measurement (S623). The notification may include a stress measurement start command. The second electronic device 620 may display a fifth user interface 722 indicating that the stress is being measured, during measuring of the stress of the user.

When the first electronic device 610 receives the ending input of the meditation program directly from the user or from the second electronic device 620, the first electronic device 610 may end the meditation program (S614). The first electronic device 610 may transmit the ending notification of the meditation program to the second electronic device 620. When the ending input of the meditation program is received by the second electronic device 620, the ending notification transmission operation S615 may be omitted.

When the second electronic device 620 identifies the ending notification of the meditation program, the second electronic device 620 may end the stress measurement of the user (S624). The second electronic device 620 may synchronize the stress data measured during the meditation program execution with the first electronic device 610 (S625).

The first electronic device 610 may receive the measured stress data from the second electronic device 620. The first electronic device 610 may display the received stress data (S616). The first electronic device 610 may provide a third user interface 713 including visual information 7131 that visually indicates the result of the measurement of the user's stress change while the meditation program is executed.

In FIG. 6, it is shown that after the end of the stress measurement, the second electronic device 620 synchronizes the measured stress data with the first electronic device 610 (S625). However, according to an embodiment, the stress data measured in the second electronic device 620 may be synchronized with the first electronic device 610 in real time. Further, according to an embodiment, the first electronic device 610 may display the stress data synchronized in real time to the user in real time.

According to an embodiment, when the first electronic device 610 is an electronic device that may continuously measure the stress of the user, all of the above-described operations executed in the second electronic device 620 may be executed in the first electronic device 610.

The order of the operations of the flowchart 600 shown in FIG. 6 may be changed according to other embodiments, as explained above. Also as explained above, some operations thereof may be omitted.

Hereinafter, with reference to FIG. 8 and FIG. 9, an operation method of the electronic device according to an embodiment will be described. Descriptions of the same configuration and operation as in the above-described embodiment may be omitted.

Figure 8:
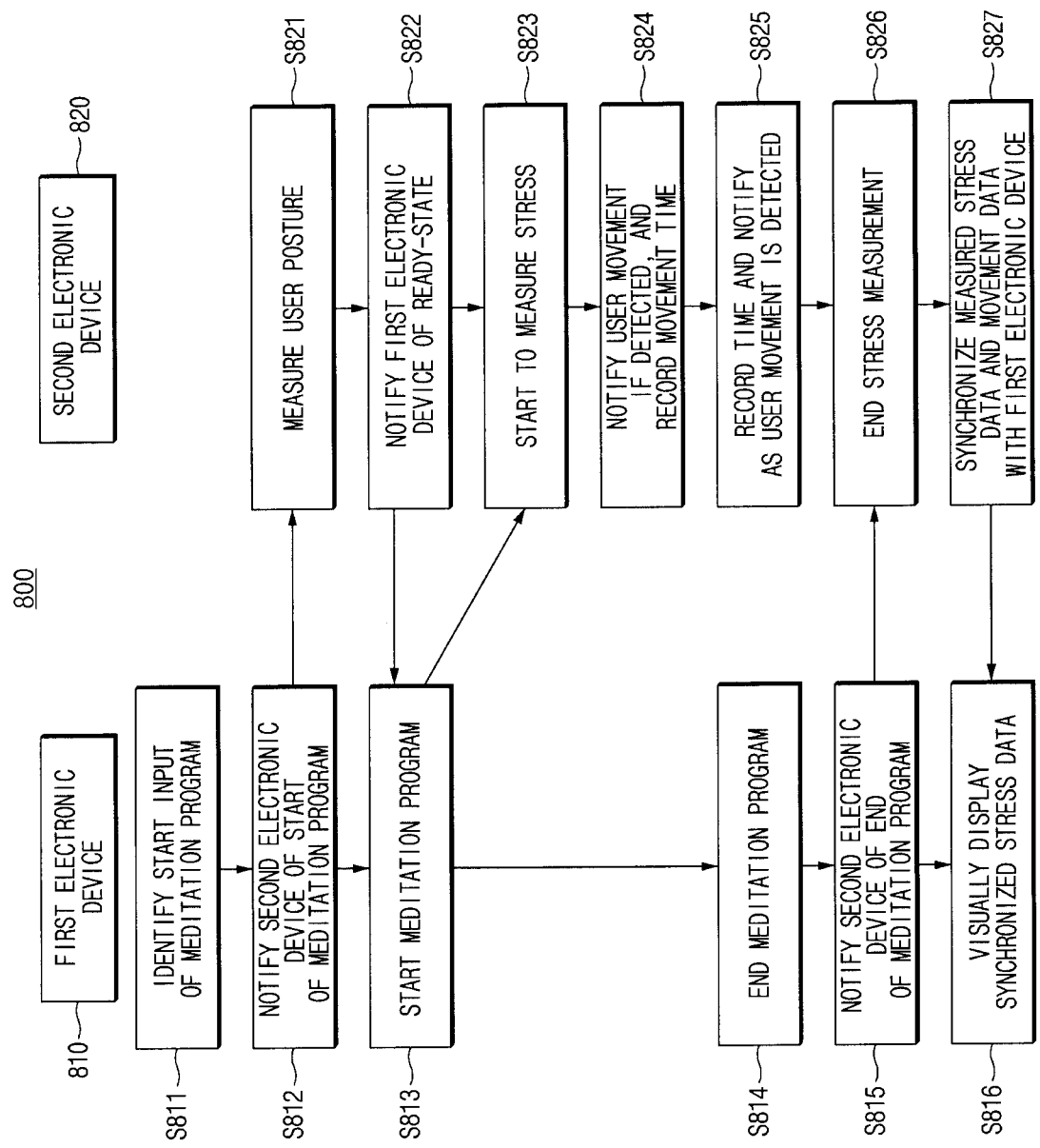
FIG. 8 is a flowchart illustrating a method of operating an electronic device according to an embodiment.

FIG. 8 is a flowchart 800 showing an operation method of an electronic device according to an embodiment. FIG. 9 is a diagram 900 illustrating a user interface of an electronic device according to an embodiment in a sequence of operations as disclosed in FIG. 8.

Figure 9:
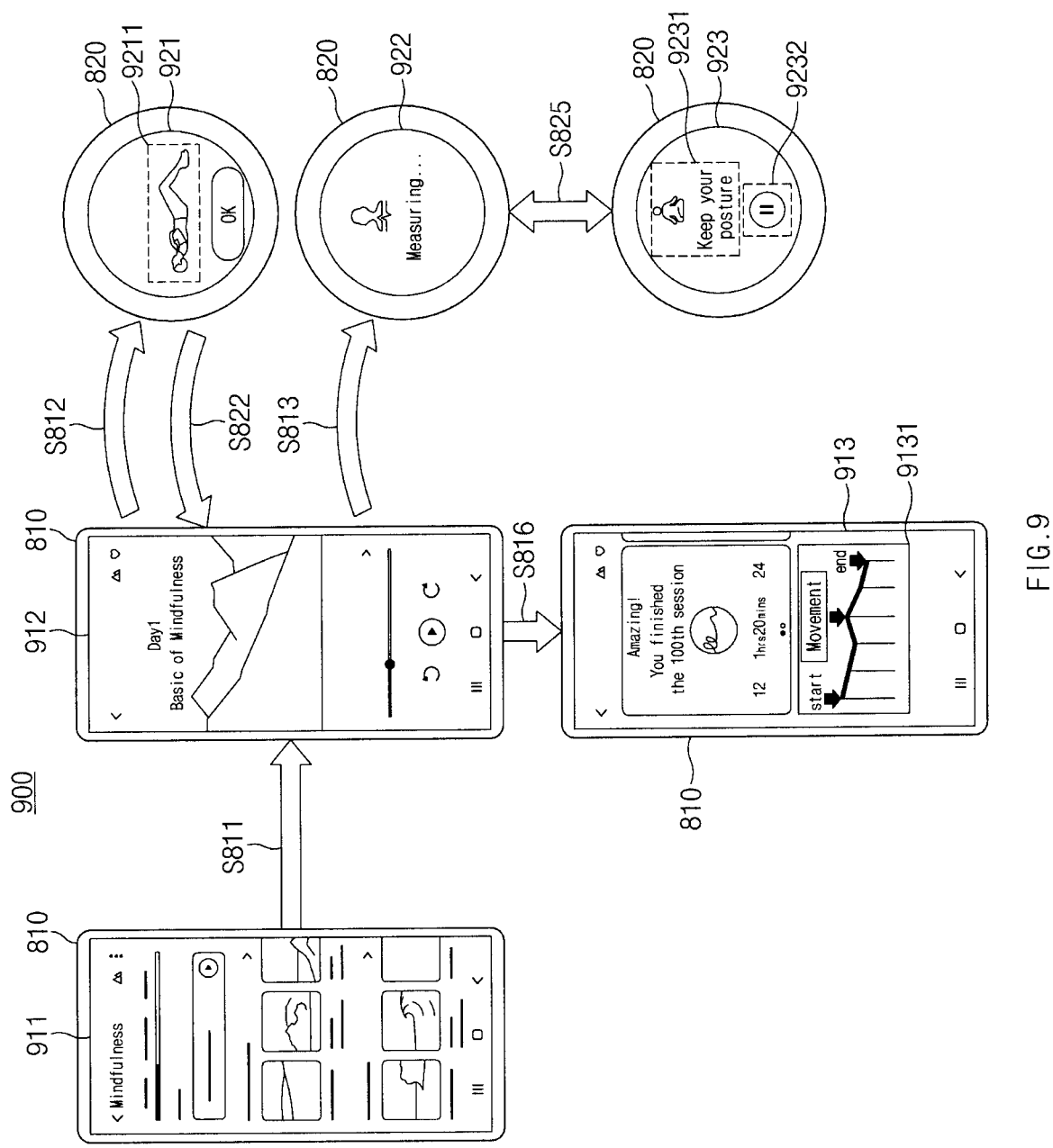
FIG. 9 is a diagram illustrating a user interface, shown in relation to a sequence of operations, of an electronic device according to an embodiment.

Referring to FIG. 8 and FIG. 9, a first electronic device 810 (e.g., the electronic device 101 of FIG. 1, the electronic device 300 of FIG. 3A, the first electronic device 410 of FIG. 4 or the first electronic device 610 of FIG. 6) may identify the start input of the user's meditation program (S811). The start input of the meditation program is received via a first user interface 911 of the first electronic device 810. Alternatively, when a second electronic device 820 (e.g., the first or second wearable electronic device 102 or 104 of FIG. 1, the second electronic device 420 of FIG. 4 or the second electronic device 620 of FIG. 6) includes a user interface to receive the start input of the meditation program, the start input may be received via the user interface of the second electronic device 820.

When the first electronic device 810 identifies the start input of the meditation program, the first electronic device 810 may send the start notification of the meditation program to the second electronic device 820. When the start input of the meditation program is received by the second electronic device 820, the start notification transmission operation S812 may be omitted.

When identifying the start notification of the meditation program, the second electronic device 820 may start posture measurement of the user (S821). According to an embodiment, the second electronic device 820 may display a fourth user interface 921 displaying guide information 9211 for guiding a posture suitable for meditation.

When the second electronic device 820 identifies that the posture of the user is stable and suitable for meditation, the second electronic device 820 may send a ready-to-start notification to the first electronic device 810 (S822). Alternatively, when the second electronic device 820 receives an input indicating that the user is ready for meditation from the user via the fourth user interface 921, the second electronic device 820 may send the ready-to-start notification to the first electronic device 810. The first electronic device 810 and the second electronic device 820 may allow the user to start the meditation program only when a stable posture is achieved to maximize stress reduction.

When the first electronic device 810 receives the ready-to-start notification from the second electronic device 820, the first electronic device 810 may start the meditation program (S813). The first electronic device 810 may provide a second user interface 912 that displays the meditation program for the start of the meditation program.

When the second electronic device 820 receives a notification indicating that the meditation program has been started from the first electronic device 810, the second electronic device 820 may start the user's stress measurement (S823). The second electronic device 820 may display a fifth user interface 922 indicating that the stress is being measured, during when the stress of the user is measured.

The second electronic device 820 may measure whether the user has moved during the meditation program execution (S824). When user's movement is detected during the meditation program execution, the second electronic device 820 may display a sixth user interface 923 that displays a notification to the user to maintain the posture suitable for meditation. The sixth user interface 923 may include guide information 9231 for the meditation posture along with the posture maintenance notification. The second electronic device 820 may detect the user's movement during the meditation program execution and prompt the user to return to a stable posture to maximize the effect of the meditation program.

Further, when the movement of the user is detected during the meditation program execution, the second electronic device 820 may record the time interval in which the user moved, together with the stress measurement result (S825).

When the first electronic device 810 receives the ending input of the meditation program directly from the user or from the second electronic device 820, the first electronic device 810 may end the meditation program S814. The first electronic device 810 may transmit the ending notification of the meditation program to the second electronic device 820.

When the ending input of the meditation program is received by the second electronic device 820, the ending notification transmission operation S815 may be omitted. According to an embodiment, the sixth user interface 923 of the second electronic device 820 may include a pause button 9232. In this connection, the ending input of the meditation program may correspond to a touch of the pause button 9232 of the sixth user interface 923 of the second electronic device 820.

When the second electronic device 820 identifies the ending notification of the meditation program, the second electronic device 820 may end the user's stress measurement (S826). The second electronic device 820 may synchronize the stress data measured during the meditation program execution, and the record of the time point of the user's movement with the first electronic device 810 (S827).

The first electronic device 810 may receive the measured data from the second electronic device 820. The first electronic device 810 may display the received data (S816).

The first electronic device 810 may provide a third user interface 913 displaying visual information 9131 visually indicating the result of measuring the stress change of the user while the meditation program is executed. The first electronic device 810 may analyze the data received from the second electronic device 820 and thus display a graph of the stress change of the user while the meditation program is executed. The first electronic device 810 may display a start time and an end time of the meditation program on the graph so as to indicate to the user the stress change during the meditation program execution. Further, the first electronic device 810 may analyze the received data and display a user interface element indicating when the user moved during the execution of the meditation program on the graph. Thus, the user may be able to identify how the user movement during the meditation program execution affected the stress level of the user. Further, when the user changes the meditation posture during the meditation program execution, the user may identify which posture is most effective in reducing stress level based on the graph that shows when the user moved.

The order of the operations of the flowchart 800 shown in FIG. 8 may be changed according to other embodiments, as explained above. Also as explained above, some operations thereof may be omitted.

In FIG. 8 it is shown that after the ending of the stress measurement, the second electronic device 820 synchronizes the measured stress data with the first electronic device 810 (S827). However, according to another embodiments, the stress data measured by the second electronic device 820 may be synchronized with the first electronic device 810 in real time. Further, according to an embodiment, the first electronic device 810 may display the stress data synchronized in real time to the user in real time.

Further, according to one embodiment, the second electronic device 820 may measure the stress of the user continuously or periodically when the meditation program is not being executed. When the second electronic device 820 determines that the user's measured stress is above a certain numerical value (threshold value), or determines, based on a measured stress trend of the user, that the stress value will reach a certain numerical value (threshold value) within a certain period, the second electronic device 820 may transmit the determination result to the first electronic device 810. Alternatively, the second electronic device 820 may transmit the measured stress to the first electronic device 810 in real time. Then, the first electronic device 810 may determine, based on the stress value received from the second electronic device 820 in real time, whether the user's measured stress is above a certain numerical value (threshold value), or determines, based on a measured stress trend of the user, whether the stress value will reach a certain numerical value (threshold value) within a certain period.

When the user's measured stress is above a certain numerical value (threshold value), or when the stress value will reach a certain numerical value (threshold value) within a certain period, the first electronic device 810 may recommend a meditation program. The first electronic device 810 may display a user interface recommending a meditation program. According to an embodiment, the first electronic device 810 may transmit information about the recommended meditation program to the second electronic device 820. The second electronic device 820 may display a user interface recommending the meditation program.

According to an embodiment, the recommendation of the meditation program may include a recommendation of a personalized meditation program based on the previous meditation program execution record of the user. The first electronic device 810 may store the user's previous meditation program execution record therein. The first electronic device 810 may recommend a meditation program that has excellent stress reduction effect for this particular user based on the user's previous meditation program execution record. Because the first electronic device 810 receives and stores therein the change trend result of the stress of the user as measured by the second electronic device 820 during the execution of the meditation program, the first electronic device 810 may select a meditation program that has the best stress reduction effect.

Further, according to an embodiment, the first electronic device 810 may determine a current location or state of the user and recommend the meditation program based on the current location or state. The current location or state of the user may be measured directly using the sensor module included in the first electronic device 810. Alternatively, the first electronic device 810 receives the location or state result measured by the sensor module included in the second electronic device 820.

For example, when the current location of the user is the user's home, the first electronic device 810 may recommend the meditation program because home is an appropriate location for meditation. When the user is outdoors, the first electronic device 810 may not recommend the meditation program because the outdoors is not an appropriate location.

Further, according to one embodiment, the first electronic device 810 may recommend a meditation program suitable for sitting posture when the user's measured posture is the sitting posture. When the user is standing, the first electronic device 810 may recommend a meditation program suitable for the standing posture. Further, the first electronic device 810 may recommend a meditation program based a combination of the user's location and posture.

Further, according to one embodiment, the first electronic device 810 may provide various combinations of audio and posture in the meditation programs based on target effects. For example, a first program may provide a posture "A" and an audio "a", and a second program may provide a posture "B" and an audio "b." The first electronic device 810 may recommend the combination of "A" and "b" or the combination of "B" and "a" as the meditation program, based on target effects of the meditation programs. The first electronic device 810 may store, therein, execution results of the meditation programs. The first electronic device 810 may compare the stored execution results of the meditation programs with each other, and configure the most efficient program for the user based on the comparison result, and thus recommend a personalized meditation program to the user. The video, audio and posture of the meditation programs may be mixed and matched and thus a combination may be recommended to the user.

Further, according to an embodiment, the first electronic device 810 may analyze an appropriate meditation time period required to reduce the stress and recommend a meditation program based on the appropriate meditation time period. The appropriate meditation time period may be analyzed based on the user's meditation program execution record.

Further, according to an embodiment, after the meditation program starts, the first electronic device 810 may analyze the stress measurement data received in real time from the second electronic device 820. Then, when it is determined based on the analysis that the reduction of the stress using the currently executing mediation program is not sufficient, the first electronic device 810 may recommend another meditation program besides the currently executing mediation program.

Further, according to one embodiment, when the first electronic device 810 is connected to a lighting device over IoT (Internet of Things), the first electronic device 810 may turn off the lighting device or dim the lighting device to maximize meditation efficiency. Further, according to one embodiment, when the first electronic device 810 is connected to a speaker over IoT (Internet of Things), the first electronic device 810 may play audio included in the meditation program via the speaker or adjust the volume of the speaker to an appropriate level. Further, according to one embodiment, when the first electronic device 810 is connected to a TV over IoT, the first electronic device 810 may play video included in the meditation program on the TV.

Further, according to an embodiment, when the stress of the user received after the meditation program starts is very high, the first electronic device 810 may automatically switch to an interfering-prohibition mode to maximize the meditation efficiency. The interfering-prohibition mode may correspond to a silent mode of the first electronic device 810.

According to an embodiment, when the first electronic device 810 is an electronic device that may continuously measure the stress of the user, all of the above-described operations executed in the second electronic device 820 may be executed in the first electronic device 810.

Hereinafter, referring to FIG. 1, FIG. 2 and FIG. 10A to FIG. 10C, a structure of the second electronic device according to an embodiment of the disclosure will be described.

Figure 10A:
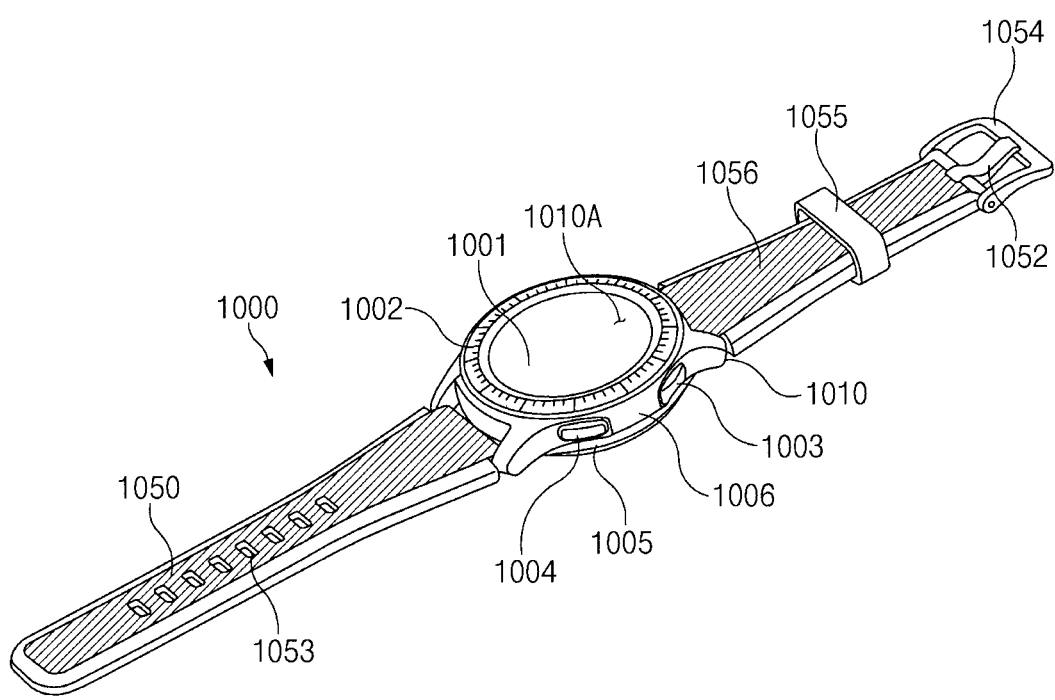
FIG. 10A is a perspective view of a front face of an electronic device according to an embodiment.
Figure 10B:
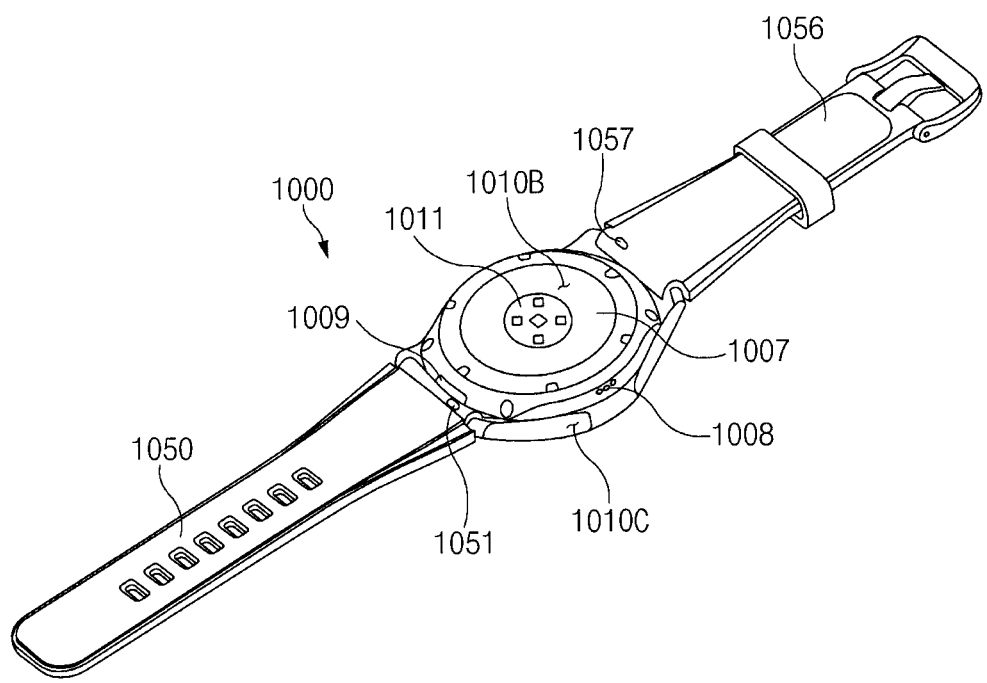
FIG. 10B is a perspective view of a rear face of the electronic device of FIG. 10A.
Figure 10C:
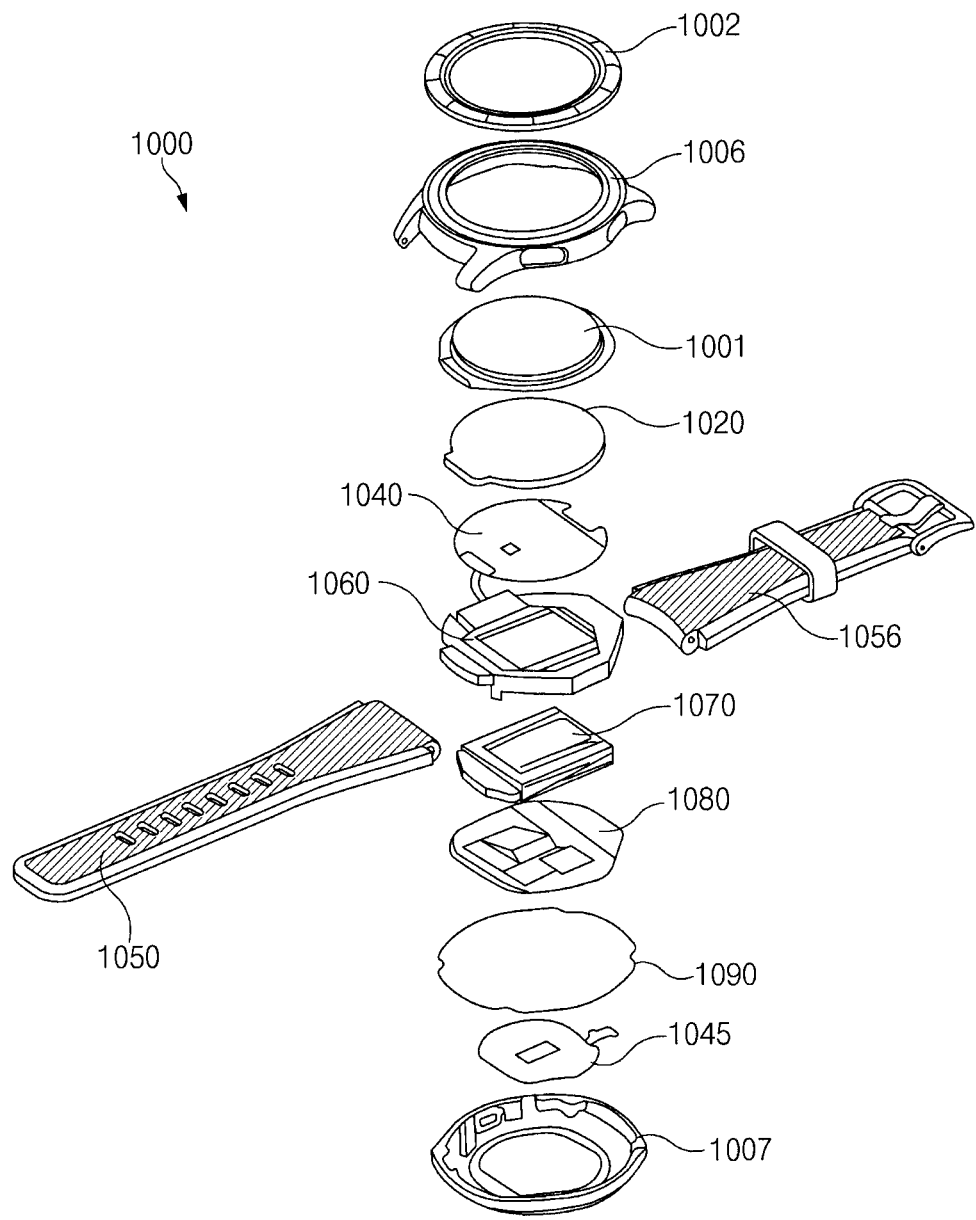
FIG. 10C is an exploded perspective view of the electronic device of FIG. 10A.

FIG. 10A is a perspective view of a front surface of the electronic device according to an embodiment. FIG. 10B is a perspective view of a rear surface of the electronic device of FIG. 10A. FIG. 10C is an exploded perspective view of the electronic device of FIG. 10A.

Referring to FIG. 1 and FIG. 10A to FIG. 10C, a second electronic device 1000 of FIGS. 10A to 10C may correspond to either the first wearable electronic device 102 or the second wearable electronic device 104 of FIG. 1. The second electronic device 1000 may communicate with the first electronic device 101 in a wired manner or wirelessly and may communicate with the first electronic device 101 over a short-range or a long-range. The first electronic device 101 and the second electronic device 1000 may be identical or similar to each other in terms of configurations and functions. Descriptions of components included in the second electronic device 1000 may be omitted since the descriptions may be the same as the descriptions of the components included in the first electronic device 101 with reference to FIG. 1.

Referring to FIG. 10A to FIG. 10C, the second electronic device 1000 according to an embodiment may include a housing 1010 including a first surface or front surface 1010A, a second surface or rear surface 1010B, and a side surface 1010C surrounding a space between the first surface 1010A and the second surface 1010B, and attachment members 1050 and 1056 connected to at least a portion of the housing 1010 and configured to detachably attach the second electronic device 1000 to a user's body part (e.g., wrist, ankle). In another embodiment (not shown), the housing may refer to a structure that defines a portion of each of the first surface 1010A, the second surface 1010B, and the side surface 1010C of FIG. 1. According to one embodiment, the first surface 1010A may be formed of a front plate 1001 (such as a glass plate or a polymer plate including various coating layers) which is at least partially substantially transparent. The second surface 1010B may be formed of a substantially opaque rear plate 1007. The rear plate 1007 may be made, for example, of a coated or colored glass, ceramic, polymer, metal (such as aluminum, stainless steel (STS), or magnesium), or a combination of at least two of the materials. The side surface 1010C may be combined with the front plate 1001 and the rear plate 1007 and may be formed of a side bezel structure 1006 (or "side member") made of metal and/or polymer. In some embodiments, the rear plate 1007 and side bezel structure 1006 may be integrally formed with each other and include the same material (such as a metal material such as aluminum). Each of the attachment members 1050 and 1056 may be made of various materials and may have various shapes. Each of the attachment members 1050 and 1056 may be made of a woven fabric, leather, rubber, urethane, metal, ceramic, or a combination of at least two of the materials such that each of the attachment members 1050 and 1056 may be monolithic in a flexible manner or have a plurality of links in an articulated manner.

According to one embodiment, the second electronic device 1000 may include at least one of a display 1020 (see FIG. 3), audio modules 1005 and 1008, a sensor module 1011, key input devices 1002, 1003, and 1004, and a connector hole 1009. In some embodiments, the second electronic device 1000 may be free of at least one of the components (e.g., the key input device 1002, 1003 and 1004 or the connector hole 1009) or may additionally include other components.

The display 1020 may be exposed through, for example, a substantial portion of the front plate 1001. A shape of the display 1020 may correspond to a shape of the front plate 1001 and may be various shapes such as circular, oval, or polygonal shape. The display 1020 may be coupled to or adjacent to a touch sensing circuit, a pressure sensor that may measure an intensity (pressure) of a touch, and/or a fingerprint sensor.

The audio module 1005 and 1008 may include the microphone hole 1005 and the speaker hole 1008. The microphone hole 1005 may contain a microphone for acquiring an external sound. In some embodiments, a plurality of microphones may be arranged to sense a direction of a sound. The speaker hole 1008 may be used as an external speaker and a call receiver. In some embodiments, the speaker hole 1008 and a microphone hole 1005 may be combined into a single hole, or the speaker may be included without the speaker hole 1008 (for example, piezo speaker).

The sensor module 1011 may generate an electrical signal or data value corresponding to an internal operating state of the second electronic device 1000 or an external environmental state thereof. At least one sensor of the sensor module including the sensor module 1011 may be disposed on the second surface 1010B of the housing 1010. The at least one sensor module disposed on the second surface 1010B of the housing 1010 may be a sensor associated with a user's biometrics. The second electronic device 1000 may further include a sensor module not shown in the figure.

Referring to FIG. 1, FIG. 2 and FIG. 10A to FIG. 10C, the sensor module 1011 included in the second electronic device 1000 may have the same or similar configuration and function as or to those of the sensor module 176 included in the first electronic device 101. A description of the sensor module 1011 included in the second electronic device 1000 may be omitted since the description thereof may be the same as the description of the sensor module 176 included in the first electronic device 101 with reference to FIG. 2.

Referring back to FIG. 10A to FIG. 10C, the key input device 1002, 1003, and 1004 may include the wheel key 1002 disposed on the first surface 1010A of the housing 1010 and rotatable in at least one direction, and/or the side key buttons 1002 and 1003 disposed on the side surface 1010C of the housing 1010. The wheel key 1002 may have a shape corresponding to that of the front plate 1001. In another embodiment, the second electronic device 1000 may not include some or all of the mentioned key input devices 1002, 1003, and 1004. The key input devices 1002, 1003, and 1004 that are not included in the second electronic device 1000 may be implemented in other forms such as soft keys on the display 1020.

The connector hole 1009 may accommodate a first connector hole configured for accommodating a connector (e.g., USB connector) for transmitting and receiving power and/or data with an external electronic device, and/or a second connector hole (not shown) which may accommodate a connector for transmitting and receiving an audio signal with an external electronic device. The second electronic device 1000 may further include a connector cover (not shown) to cover, for example, at least a portion of the connector hole 1009 and block incoming of an foreign matter into the connector hole.

Each of the attachment members 1050 and 1056 may be detachably attached to at least a portion of the housing 1010 via each of locking members 1051 and 1057. The attachment members 1050 and 1056 may include one or more of a fixing member 1052, a fixing member fastening hole 1053, a band guide member 1054, and a band fixing ring 1055.

The fixing member 1052 may be configured to fix the housing 1010 and the attachment members 1050 and 1056 to a user's body part (e.g., wrist, ankle). The fixing member fastening hole 1053 may receive the fixing member 1052 to fix the housing 1010 and attachment members 1050 and 1056 to the user's body part. The band guide member 1054 may be configured to limit a movement range of the fixing member 1052 when the fixing member fastening hole 1053 receives the fixing member 1052, such that the attachment members 1050 and 1056 may be in close contact with the user's body part. The band fixing ring 1055 may limit a range of movement of the attachment members 1050 and 1056 while the fixing member 1052 is inserted into the fixing member fastening hole 1053.

The second electronic device 1000 may include the side bezel structure 1006, the wheel key 1002, the front plate 1001, the display 1020, a first antenna 1040, a second antenna 1045, a support member 1060 (e.g. bracket), a battery 1070, a printed circuit board 1080, a sealing member 1090, the rear plate 1007, and the attachment member 1050 and 1056.

The support member 1060 may be disposed inside the electronic device 1000 and may be connected to the side bezel structure 1006, or may be integrally formed with the side bezel structure 1006. The support member 1060 may be made of, for example, a metal material and/or a nonmetallic material such as a polymer material. The support member 1060 may have one face coupled to the display 1020 and the other face coupled to the printed circuit board 1080. On the printed circuit board 1080, a processor, a memory, and/or an interface may be mounted. The processor may include, for example, one or more of a central processing unit, an application processor, a GPU (graphic processing unit), a sensor processor, or a communication processor.

The memory may include, for example, a volatile memory or a nonvolatile memory. The interface may include, for example, an HDMI (high definition multimedia interface), a USB (universal serial bus) interface, an SD card interface, and/or an audio interface. The interface may, for example, electrically or physically connect the electronic device 300 to an external electronic device. The interface may include an USB connector, a SD card/MMC connector, or an audio connector.

The battery 1070 refers to a device for powering at least one component of the second electronic device 1000, and may include, for example, a non-rechargeable primary cell, or a rechargeable secondary cell, or a fuel cell. At least a portion of the battery 1070 may be substantially coplanar with, for example, the printed circuit board 1080. The battery 1070 may be integrally with and disposed inside the second electronic device 1000 or may be detachable from the second electronic device 1000.

The first antenna 1040 may be disposed between the display 1020 and the support member 1060. The first antenna 1040 may include, for example, an NFC (near field communication) antenna, a wireless charging antenna, and/or an MST (magnetic secure transmission) antenna. The first antenna 1040 may, for example, perform short-range communication with an external device or wirelessly transmit and receive power required for charging of the second electronic device 1000 or transmit a self-based signal including a short range communication signal or payment data. In another embodiment, the first antenna 1040 may have an antenna structure formed by a portion of the side bezel structure 1006 and/or the support member 1060 or a combination thereof.

The second antenna 1045 may be disposed between the printed circuit board 1080 and the rear plate 1007. The second antenna 1045 may include, for example, an NFC (near field communication antenna), a wireless charging antenna, and/or an MST (magnetic secure transmission) antenna. The second antenna 1045 may, for example, perform short-range communication with an external device or wirelessly transmit and receive power required for charging of the second electronic device 1000 or transmit a self-based signal including a short range communication signal or payment data. In another embodiment, the second antenna 1045 may have an antenna structure formed by a portion of the side bezel structure 1006 and/or the rear plate 1007 or a combination thereof.

The sealing member 1090 may be located between the side bezel structure 1006 and the rear plate 1007. The sealing member 1090 may be configured to prevent moisture and foreign matter from an outside from entering a space surrounded by the side bezel structure 1006 and the rear plate 1007.

The shape of the second electronic device 1000 is not limited to FIG. 10A to FIG. 10C. According to an embodiment, the shape of the second electronic device 1000 may be whatever is appropriate for a wearable device. For example, the second electronic device 1000 may be an audio device that is worn on the ear. When the second electronic device 1000 is an audio device, the second electronic device 1000 may be worn on the user's ear to measure biometric information of the user. Thus, the second electronic device 1000 may continue to measure stress while the user is wearing the second electronic device 1000 as the audio device. Further, while the user wears the audio device, the audio device may play information (audio) of the meditation program by itself or may receive and play the same from the first electronic device 101. Further, the audio device may measure whether the user is wearing the audio device and, accordingly, recommend another meditation program or vary the meditation program execution. In this connection, the recommendation or execution of the meditation program may be directly performed by the audio device or may be performed by the audio device based on related information received from the first electronic device. For example, when it is determined that a user wears the audio device at home, the audio device may guide execution of the meditation program. Alternatively, for example, when the user is not wearing the audio device at home, the audio device may guide the meditation program via other wearable devices or other electronic devices such as AI speakers, TVs, or mobiles.

Hereinafter, with reference to FIG. 11, an operation method of the electronic device according to an embodiment will be described. Description of the same configuration and operation as in the above-described embodiment may be omitted.

Figure 11:
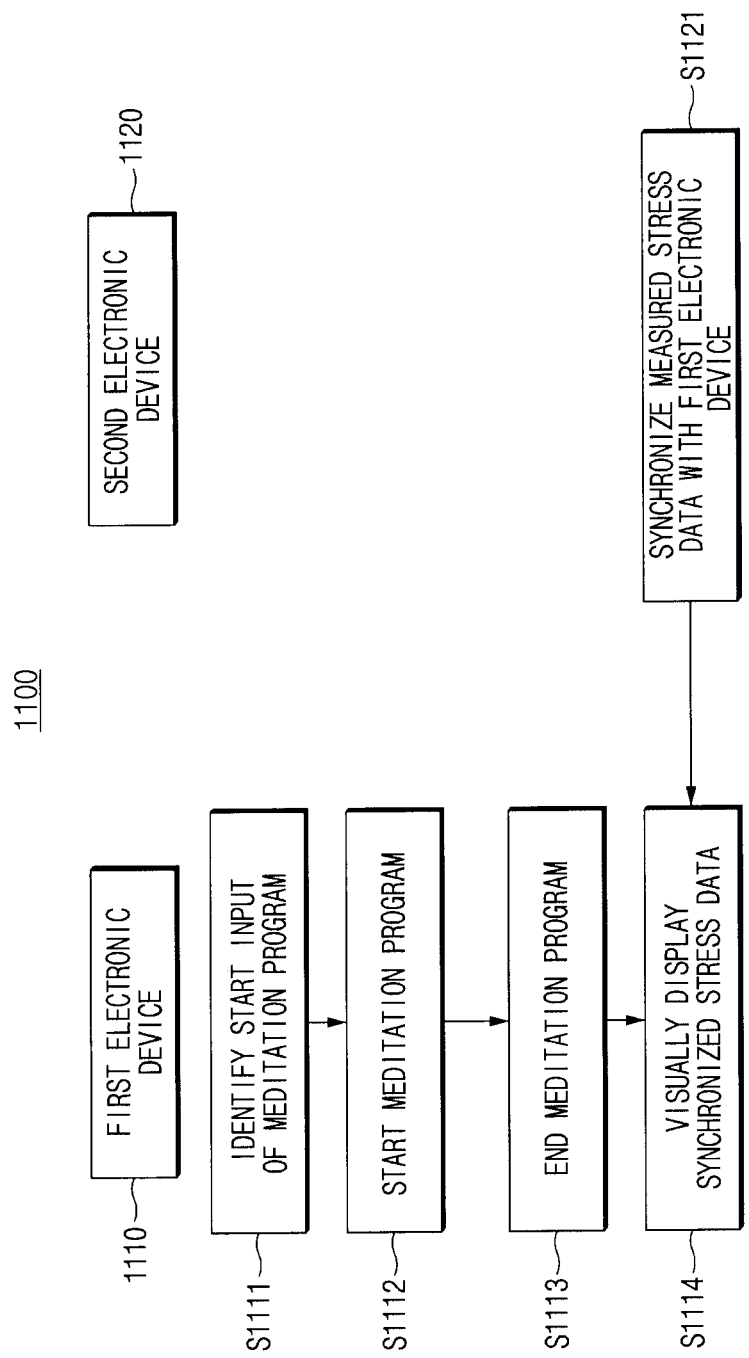
FIG. 11 is a flowchart illustrating a method of operating an electronic device according to an embodiment.

FIG. 11 is a flow chart 1100 showing an operation method of an electronic device according to an embodiment.

Referring to FIG. 11, a first electronic device 1110 (e.g., the electronic device 101 of FIG. 1 or the electronic device 300 of FIG. 3A) may identify the user's start input of the meditation program (S1111).

Although not shown in FIG. 11, when the first electronic device 1110 identifies the start input of the meditation program, the first electronic device 1110 may send the start notification of the meditation program to a second electronic device 1120 (e.g., the first or second wearable electronic device 102 or 104 in FIG. 1) (not shown in FIG. 11).

When the first electronic device 1110 identifies the start input of the meditation program, the first electronic device 1110 may start the meditation program (S1112).

When the first electronic device 1110 identifies the ending input of the user, the first electronic device 1110 may end the meditation program (S1113).

Although not shown in FIG. 11, when the first electronic device 1110 identifies the meditation program ending input of the user, the first electronic device 1110 may transmit the ending notification of the meditation program to the second electronic device 1120.

The second electronic device 1120 may transmit the measured stress data during the execution of the meditation program to the first electronic device 1110 (S1121). The second electronic device 1120 may know the start time and the end time of the meditation program based on the start notification and the ending notification received from the first electronic device 1110. The second electronic device 1120 may transmit the stress data of the user from the start of the meditation program to the end of the meditation program to the first electronic device 1110.

The first electronic device 1110 may receive the measured stress data from the second electronic device 1120. The first electronic device 1110 may visualize and display the received stress data (S1114).

According to certain embodiments disclosed in the disclosure, an electronic device for visually presenting a stress change according to an execution of a meditation program may be provided.

According to certain embodiments disclosed in the disclosure, an electronic device for measuring a stress change according to an execution of a meditation program during the execution of the meditation program and presenting the measured stress change may be provided.

According to certain embodiments disclosed in the disclosure, an electronic device for recommending a meditation program according to a user's location, posture, stress level, and/or meditation execution record may be provided.

According to certain embodiments disclosed in the disclosure, an electronic device for measuring a posture or movement of a user and inducing a posture for meditation before or during a meditation program execution may be provided.

According to certain embodiments disclosed in the disclosure, an electronic device for guiding a posture of a user such that the posture is induced to be suitable for meditation may be provided.

According to certain embodiments disclosed in the disclosure, an electronic device that may maximize a reduction of a stress of a user using a meditation program may be provided.

In addition, various effects that are identified directly or indirectly from the disclosure may be provided.

While the disclosure has been shown and described with reference to various embodiments thereof, it will be understood by those skilled in the art that various changes in form and details may be made therein without departing from the spirit and scope of the disclosure as defined by the appended claims and their equivalents.

Certain of the above-described embodiments of the present disclosure can be implemented in hardware, firmware or via the execution of software or computer code that can be stored in a recording medium such as a CD ROM, a Digital Versatile Disc (DVD), a magnetic tape, a RAM, a floppy disk, a hard disk, or a magneto-optical disk or computer code downloaded over a network originally stored on a remote recording medium or a non-transitory machine readable medium and to be stored on a local recording medium, so that the methods described herein can be rendered via such software that is stored on the recording medium using a general purpose computer, or a special processor or in programmable or dedicated hardware, such as an ASIC or FPGA. As would be understood in the art, the computer, the processor, microprocessor controller or the programmable hardware include memory components, e.g., RAM, ROM, Flash, etc. that may store or receive software or computer code that when accessed and executed by the computer, processor or hardware implement the processing methods described herein.

What is claimed is:

1. An electronic device comprising:
    a processor;
    a biometric sensor;
    a motion sensor; and
    a memory electrically connected to the processor;
    wherein the memory stores instructions that, when executed by the processor, cause the electronic device to:
        identify a user input to start a meditation program;
        start the meditation program in response to the identified user input;
        obtain data related to a stress level of a user measured by the biometric sensor during execution of the meditation program;
        determine, based on the obtained data, whether a stress level reduction effect by the meditation program is below a predefined reference value;
        in response to determining that the stress level reduction effect by the meditation program is below the predefined reference value, determine a posture of the user based on another data obtained by the motion sensor; and
        recommend another meditation program corresponding to the determined posture, wherein the determined posture is a lotus posture, a standing posture, a lying down posture, or a sitting posture.

2. The electronic device of claim 1, wherein the data related to the stress level is continuously measured during the execution of the meditation program.

3. The electronic device of claim 1, wherein the instructions, when executed by the processor, cause the electronic device to:
    display visual information on a display included in the electronic device, and
    wherein the visual information visually indicates a stress level change of the user resulting from the execution of the meditation program, based on the data.

4. The electronic device of claim 3, wherein the visual information includes a result of comparing the stress level of the user at a start of the meditation program to the stress level of the user at an end of the meditation program.

5. The electronic device of claim 1, wherein the instructions, when executed by the processor, cause the electronic device to:
    obtain movement data using the motion sensor, the movement data including data indicating a time when a movement of the user is detected during the execution of the meditation program,
    display visual information on a display included in the electronic device, wherein the visual information includes a graph indicating a stress level change of the user during the execution of the meditation program, and the time included in the movement data.

6. The electronic device of claim 1, wherein the instructions, when executed by the processor, cause the electronic device to:
    obtain another data related to the stress level of the user measured by the biometric sensor while a meditation application for executing the meditation program is not executed;
    determine, based on the other data related to the stress level, whether the stress level of the user reaches a threshold value or whether the stress level of the user will reach the threshold value within a predetermined time period; and
    recommend at least one meditation program based on the determination that the stress level of the user reaches the threshold value or the stress level of the user will reach the threshold value within the predetermined time period.

7. The electronic device of claim 1, wherein the instructions, when executed by the processor, cause the electronic device to:

select one of a plurality of audios and one of a plurality of postures based on an execution record of at least one meditation program that is previously executed by the user; and recommend a personalized meditation program based on a combination of the selected one of the plurality of audios and the selected one of the plurality of postures.

8. The electronic device of claim 1, wherein the electronic device further includes a position sensor, wherein the instructions, when executed by the processor, cause the electronic device to recommend at least one meditation program based on a position of the user measured by the position sensor.

9. A method for providing a meditation program by an electronic device, the method comprising:

identifying a user input to start a meditation program;

starting the meditation program in response to the identified user input;

obtaining data related to a stress level of a user measured by a biometric sensor of the electronic device during execution of the meditation program;

determining, based on the obtained data, whether a stress level reduction effect by the meditation program is below a predefined reference value; and in response to determining that the stress level reduction effect by the meditation program is below the predefined reference value, determining a posture of the user based on another data obtained by a motion sensor of the electronic device; and recommending another meditation program corresponding to the determined posture, wherein the determined posture is a lotus posture, a standing posture, a lying down posture, or a sitting posture.

10. The method of claim 9, wherein the data related to the stress level is continuously measured during the execution of the meditation program.

11. The method of claim 9, further comprising:

displaying visual information on a display of the electronic device, wherein the visual information visually indicates a stress level change of the user resulting from the execution of the meditation program, based on the data.

12. The method of claim 11, wherein the visual information includes a result of comparing the stress level of the user at a start of the meditation program to the stress level of the user at an end of the meditation program.

13. The method of claim 9, further comprising:

obtaining movement data using the motion sensor, the movement data including data indicating a time when a movement of the user is detected during the execution of the meditation program, displaying visual information on the display, wherein the visual information includes a graph indicating a stress level change of the user during the execution of the meditation program, and the time included in the movement data.

14. The method of claim 9, further comprising:

obtaining another data related to the stress level of the user measured by the biometric sensor while a meditation application for executing the meditation program is not executed;

determining, based on the other data related to the stress level, whether the stress level of the user reaches a threshold value or whether the stress level of the user will reach the threshold value within a predetermined time period; and recommending at least one meditation program based on the determination that the stress level of the user reaches the threshold value or the stress level of the user will reach the threshold value within the predetermined time period.

15. The method of claim 9, further comprising:

selecting one of a plurality of audios and one of a plurality of postures based on an execution record of at least one meditation program that is previously executed by the user; and recommending a personalized meditation program based on a combination of the selected one of the plurality of audios and the selected one of the plurality of postures.

16. The method of claim 9, further comprising:

recommending at least one meditation program based on a position of the user measured by a position sensor of the electronic device.

* * * * *